(12) United States Patent
Jahns et al.

(10) Patent No.: US 7,744,562 B2
(45) Date of Patent: Jun. 29, 2010

(54) DEVICES AND METHODS FOR INTERSTITIAL INJECTION OF BIOLOGIC AGENTS INTO TISSUE

(75) Inventors: Scott E. Jahns, Hudson, WI (US); Gary S. Oehme, Ham Lake, MN (US); Matthew D. Bonner, Plymouth, MN (US); James R. Keogh, Maplewood, MN (US)

(73) Assignee: Medtronics, Inc., Minneapolis, MN (US)

( * ) Notice: Subject to any disclaimer, the term of this patent is extended or adjusted under 35 U.S.C. 154(b) by 727 days.

(21) Appl. No.: 11/545,197

(22) Filed: Oct. 10, 2006

(65) Prior Publication Data

US 2007/0049863 A1  Mar. 1, 2007

Related U.S. Application Data

(62) Division of application No. 10/341,743, filed on Jan. 14, 2003, now abandoned.

(51) Int. Cl.
*A61M 5/30* (2006.01)
*A61M 31/00* (2006.01)
*A61B 18/18* (2006.01)

(52) U.S. Cl. .................... 604/68; 604/500; 606/41
(58) Field of Classification Search ............... 604/500, 604/68, 152; 600/573
See application file for complete search history.

(56) References Cited

U.S. PATENT DOCUMENTS

| 1,127,948 A | 2/1915 | Wappler |
| 2,004,559 A | 6/1935 | Wappler et al. |
| 3,470,875 A | 10/1969 | Johnson et al. |
| 3,630,207 A | 12/1971 | Kahn et al. |
| 3,664,330 A | 5/1972 | Deutsch |
| 3,736,936 A | 6/1973 | Basiulis et al. |
| 3,741,211 A | 6/1973 | Vreeland |
| 3,807,403 A | 4/1974 | Stumpf et al. |

(Continued)

FOREIGN PATENT DOCUMENTS

DE        43 13 903        9/1994

(Continued)

OTHER PUBLICATIONS

ISR from PCT/US2005/043200 (dated Mar. 29, 2006) (4 pages).

(Continued)

*Primary Examiner*—Nicholas D Lucchesi
*Assistant Examiner*—Ian K Holloway
(74) *Attorney, Agent, or Firm*—Mike Jaro; Jeffrey J. Hohenshell

(57) ABSTRACT

Apparatus and methods for injecting biological agents into tissue. Devices are provided having elongate shafts and distal injection heads for transversely driving needles into tissue and injecting medical agents into the tissue through the needles. A longitudinal force directed along the shaft can be translated to a needle driving force transverse to the shaft. Some devices provide controllably variable needle penetration depth. Devices include mechanical needle drivers utilizing four link pantographs, rack and pinions, and drive yokes for driving a first needle bearing body toward a second tissue contacting body. Other devices include inflatable members for driving and retracting needles. Still other devices include magnets for biasing the needles in extended and/or retracted positions. The invention includes minimally invasive methods for epicardially injecting cardiocyte precursor cells into infarct myocardial tissue.

30 Claims, 21 Drawing Sheets

U.S. PATENT DOCUMENTS

| | | |
|---|---|---|
| 3,823,575 A | 7/1974 | Parel |
| 3,823,718 A | 7/1974 | Tromovitch |
| 3,827,436 A | 8/1974 | Stumpf et al. |
| 3,830,239 A | 8/1974 | Stumpf |
| 3,859,986 A | 1/1975 | Okada et al. |
| 3,862,627 A | 1/1975 | Hans, Sr. |
| 3,886,945 A | 6/1975 | Stumpf et al. |
| 3,901,242 A | 8/1975 | Storz |
| 3,902,501 A | 9/1975 | Citron et al. |
| 3,907,339 A | 9/1975 | Stumpf et al. |
| 3,910,277 A | 10/1975 | Zimmer |
| 3,913,581 A | 10/1975 | Ritson et al. |
| 3,924,628 A | 12/1975 | Droegemueller et al. |
| 4,018,227 A | 4/1977 | Wallach |
| 4,022,215 A | 5/1977 | Benson |
| 4,043,342 A | 8/1977 | Morrison, Jr. |
| 4,061,135 A | 12/1977 | Widran et al. |
| 4,063,560 A | 12/1977 | Thomas et al. |
| 4,072,152 A | 2/1978 | Linehan |
| 4,082,096 A | 4/1978 | Benson |
| 4,207,897 A | 6/1980 | Lloyd et al. |
| 4,248,224 A | 2/1981 | Jones |
| 4,270,549 A | 6/1981 | Heilman |
| 4,275,734 A | 6/1981 | Mitchiner |
| 4,278,090 A | 7/1981 | van Gerven |
| 4,291,707 A | 9/1981 | Heilman et al. |
| 4,312,337 A | 1/1982 | Donohue et al. |
| 4,353,371 A | 10/1982 | Cosman |
| 4,377,168 A | 3/1983 | Rzasa et al. |
| 4,492,231 A | 1/1985 | Auth |
| 4,519,389 A | 5/1985 | Gudkin et al. |
| 4,590,934 A | 5/1986 | Malis et al. |
| 4,598,698 A | 7/1986 | Siegmund |
| 4,601,290 A | 7/1986 | Effron et al. |
| 4,662,376 A | 5/1987 | Belanger |
| 4,664,110 A | 5/1987 | Schanzlin |
| 4,706,667 A | 11/1987 | Roos |
| 4,723,940 A | 2/1988 | Wiegerinck |
| 4,726,358 A | 2/1988 | Brady |
| 4,732,149 A | 3/1988 | Sutter |
| 4,735,206 A | 4/1988 | Hewson |
| 4,736,749 A | 4/1988 | Lundback |
| 4,779,611 A | 10/1988 | Grooters et al. |
| 4,802,475 A | 2/1989 | Weshahy |
| 4,815,470 A | 3/1989 | Curtis et al. |
| 4,815,478 A | 3/1989 | Buchbinder et al. |
| 4,832,048 A | 5/1989 | Cohen |
| 4,872,346 A | 10/1989 | Kelly-Fry et al. |
| 4,898,577 A | 2/1990 | Badger et al. |
| 4,916,922 A | 4/1990 | Mullens |
| 4,917,095 A | 4/1990 | Fry et al. |
| 4,928,688 A | 5/1990 | Mower |
| 4,936,281 A | 6/1990 | Stasz |
| 4,940,062 A | 7/1990 | Hampton et al. |
| 4,940,064 A | 7/1990 | Desai |
| 4,946,460 A | 8/1990 | Merry et al. |
| 4,991,578 A | 2/1991 | Cohen |
| 5,009,661 A | 4/1991 | Michelson |
| 5,013,312 A | 5/1991 | Parins et al. |
| 5,026,779 A | 6/1991 | Musch et al. |
| 5,029,574 A | 7/1991 | Shimamura et al. |
| 5,033,477 A | 7/1991 | Chin et al. |
| 5,044,165 A | 9/1991 | Linner et al. |
| 5,044,947 A | 9/1991 | Sachdeva et al. |
| 5,071,428 A | 12/1991 | Chin et al. |
| 5,076,285 A | 12/1991 | Hess et al. |
| 5,078,713 A | 1/1992 | Varney |
| 5,080,102 A | 1/1992 | Dory |
| 5,080,660 A | 1/1992 | Buelina |
| 5,083,565 A | 1/1992 | Parins et al. |
| 5,085,657 A | 2/1992 | Ben-Simhon |
| 5,087,243 A | 2/1992 | Avitall |
| H1028 H | 3/1992 | Falk et al. |
| 5,100,388 A | 3/1992 | Behl et al. |
| 5,108,390 A | 4/1992 | Potocky et al. |
| 5,116,332 A | 5/1992 | Lottick |
| 5,125,928 A | 6/1992 | Parins et al. |
| 5,147,355 A | 9/1992 | Freidman et al. |
| 5,156,149 A | 10/1992 | Hudrlik |
| 5,178,133 A | 1/1993 | Pena |
| 5,190,541 A | 3/1993 | Abele et al. |
| 5,207,674 A | 5/1993 | Hamilton |
| 5,207,691 A | 5/1993 | Nardella |
| 5,217,460 A | 6/1993 | Knopfler |
| 5,217,860 A | 6/1993 | Fahy et al. |
| 5,222,501 A | 6/1993 | Ideker et al. |
| 5,224,943 A | 7/1993 | Goddard |
| 5,228,923 A | 7/1993 | Hed |
| 5,231,995 A | 8/1993 | Desai |
| 5,232,516 A | 8/1993 | Hed |
| 5,242,441 A | 9/1993 | Avitall |
| 5,242,458 A | 9/1993 | Bendel et al. |
| 5,250,047 A | 10/1993 | Rydell |
| 5,250,075 A | 10/1993 | Badie |
| 5,254,116 A | 10/1993 | Baust et al. |
| 5,254,130 A | 10/1993 | Poncet et al. |
| 5,254,600 A | 10/1993 | Blanpied et al. |
| 5,263,493 A | 11/1993 | Avitall |
| 5,269,291 A | 12/1993 | Carter |
| 5,269,326 A | 12/1993 | Verrier |
| 5,269,780 A | 12/1993 | Roos |
| 5,275,595 A | 1/1994 | Dobak, III |
| 5,277,201 A | 1/1994 | Stern |
| 5,281,213 A | 1/1994 | Milder et al. |
| 5,281,215 A | 1/1994 | Milder |
| 5,281,216 A | 1/1994 | Klicek |
| 5,293,869 A | 3/1994 | Edwards et al. |
| 5,295,484 A | 3/1994 | Marcus et al. |
| 5,306,234 A | 4/1994 | Johnson |
| 5,309,896 A | 5/1994 | Moll et al. |
| 5,316,000 A | 5/1994 | Chapelon et al. |
| 5,317,878 A | 6/1994 | Bradshaw et al. |
| 5,318,525 A | 6/1994 | West et al. |
| 5,318,589 A | 6/1994 | Lichtman |
| 5,322,520 A | 6/1994 | Milder |
| 5,323,781 A | 6/1994 | Ideker et al. |
| 5,324,255 A | 6/1994 | Passafaro et al. |
| 5,324,284 A | 6/1994 | Imran |
| 5,324,286 A | 6/1994 | Fowler |
| 5,327,905 A | 7/1994 | Avitall |
| 5,334,181 A | 8/1994 | Rubinsky et al. |
| 5,334,193 A | 8/1994 | Nardella |
| 5,336,252 A * | 8/1994 | Cohen ........................ 607/119 |
| 5,348,554 A | 9/1994 | Imran et al. |
| 5,353,783 A | 10/1994 | Nakao et al. |
| 5,354,258 A | 10/1994 | Dory |
| 5,354,297 A | 10/1994 | Avitall |
| 5,357,956 A | 10/1994 | Nardella |
| 5,361,752 A | 11/1994 | Moll et al. |
| 5,385,148 A | 1/1995 | Lesh et al. |
| 5,387,234 A | 2/1995 | Hirschberg |
| 5,396,887 A | 3/1995 | Imran |
| 5,397,304 A | 3/1995 | Truckai |
| 5,397,339 A | 3/1995 | Desai |
| 5,400,770 A | 3/1995 | Nakao et al. |
| 5,400,783 A | 3/1995 | Pomeranz et al. |
| 5,403,309 A | 4/1995 | Coleman et al. |
| 5,403,311 A | 4/1995 | Abele et al. |
| 5,403,312 A | 4/1995 | Yates et al. |
| 5,405,376 A | 4/1995 | Mulier et al. |
| 5,409,483 A | 4/1995 | Campbell et al. |
| 5,411,529 A | 5/1995 | Hudrlik |
| 5,423,807 A | 6/1995 | Milder |
| 5,423,811 A | 6/1995 | Imran et al. |

| | | | | | |
|---|---|---|---|---|---|
| 5,423,878 A | 6/1995 | Franz | 5,595,183 A | 1/1997 | Swanson et al. |
| 5,427,119 A | 6/1995 | Swartz et al. | 5,599,350 A | 2/1997 | Schulze et al. |
| 5,429,131 A | 7/1995 | Scheinman et al. | 5,607,462 A | 3/1997 | Imran |
| 5,429,636 A | 7/1995 | Shikhman et al. | 5,611,813 A | 3/1997 | Lichtman |
| 5,431,649 A | 7/1995 | Mulier et al. | 5,617,854 A | 4/1997 | Munsif |
| 5,433,708 A | 7/1995 | Nichols et al. | 5,620,459 A | 4/1997 | Lichtman |
| 5,435,308 A | 7/1995 | Gallup et al. | 5,630,837 A | 5/1997 | Crowley |
| 5,437,651 A | 8/1995 | Todd et al. | 5,632,717 A | 5/1997 | Yoon |
| 5,438,302 A | 8/1995 | Goble | 5,637,090 A | 6/1997 | McGee et al. |
| 5,441,483 A | 8/1995 | Avitall | 5,642,736 A | 7/1997 | Avitall |
| 5,443,463 A | 8/1995 | Stern et al. | 5,643,197 A | 7/1997 | Brucker et al. |
| 5,443,470 A | 8/1995 | Stern et al. | 5,649,957 A | 7/1997 | Levin et al. |
| 5,445,638 A | 8/1995 | Rydell et al. | 5,651,378 A | 7/1997 | Matheny et al. |
| 5,449,355 A | 9/1995 | Rhum et al. | 5,655,219 A | 8/1997 | Jusa et al. |
| 5,450,843 A | 9/1995 | Moll et al. | 5,656,029 A | 8/1997 | Imran et al. |
| 5,451,223 A | 9/1995 | Ben-Simhon | 5,658,278 A | 8/1997 | Imran et al. |
| 5,452,582 A | 9/1995 | Longsworth | 5,671,747 A | 9/1997 | Connor |
| 5,452,733 A | 9/1995 | Sterman et al. | 5,672,174 A | 9/1997 | Gough et al. |
| 5,454,370 A | 10/1995 | Avitall | 5,673,695 A | 10/1997 | McGee et al. |
| 5,462,545 A | 10/1995 | Wang et al. | 5,674,220 A | 10/1997 | Fox et al. |
| 5,464,447 A | 11/1995 | Fogarty et al. | 5,676,662 A | 10/1997 | Fleischhacker et al. |
| 5,465,716 A | 11/1995 | Avitall | 5,676,692 A | 10/1997 | Sanghvi et al. |
| 5,465,717 A | 11/1995 | Imran et al. | 5,676,693 A | 10/1997 | LaFontaine |
| 5,469,853 A | 11/1995 | Law et al. | 5,678,550 A | 10/1997 | Bassen et al. |
| 5,472,441 A | 12/1995 | Edwards et al. | 5,680,860 A | 10/1997 | Imran |
| 5,472,876 A | 12/1995 | Fahy | 5,681,278 A | 10/1997 | Igo et al. |
| 5,478,309 A | 12/1995 | Sweezer et al. | 5,681,308 A | 10/1997 | Edwards et al. |
| 5,478,330 A | 12/1995 | Imran et al. | 5,683,384 A | 11/1997 | Gough et al. |
| 5,480,409 A | 1/1996 | Riza | 5,687,723 A | 11/1997 | Avitall |
| 5,486,193 A | 1/1996 | Bourne et al. | 5,687,737 A | 11/1997 | Branham et al. |
| 5,487,385 A | 1/1996 | Avitall | 5,688,267 A | 11/1997 | Panescu et al. |
| 5,487,757 A | 1/1996 | Truckai et al. | 5,688,270 A | 11/1997 | Yates et al. |
| 5,496,312 A | 3/1996 | Klicek | 5,690,611 A | 11/1997 | Swartz et al. |
| 5,497,774 A | 3/1996 | Swartz et al. | 5,693,051 A | 12/1997 | Schulze et al. |
| 5,498,248 A | 3/1996 | Milder | 5,697,536 A | 12/1997 | Eggers et al. |
| 5,500,011 A | 3/1996 | Desai | 5,697,882 A | 12/1997 | Eggers et al. |
| 5,500,012 A | 3/1996 | Brucker et al. | 5,697,925 A | 12/1997 | Taylor |
| 5,505,730 A | 4/1996 | Edwards | 5,697,927 A | 12/1997 | Imran et al. |
| 5,516,505 A | 5/1996 | McDow | 5,697,928 A | 12/1997 | Walcott et al. |
| 5,520,682 A | 5/1996 | Baust et al. | 5,702,359 A | 12/1997 | Hofmann et al. |
| 5,522,788 A | 6/1996 | Kuzmak et al. | 5,702,390 A | 12/1997 | Austin et al. |
| 5,522,870 A | 6/1996 | Ben-Zion | 5,702,438 A | 12/1997 | Avitall |
| 5,531,744 A | 7/1996 | Nardella et al. | 5,709,680 A | 1/1998 | Yates et al. |
| 5,536,267 A | 7/1996 | Edwards et al. | 5,713,942 A | 2/1998 | Stern |
| 5,545,195 A | 8/1996 | Lennox et al. | 5,716,389 A | 2/1998 | Walinsky et al. |
| 5,545,200 A | 8/1996 | West et al. | 5,716,392 A | 2/1998 | Bourgeois et al. |
| 5,549,636 A | 8/1996 | Li | 5,718,241 A | 2/1998 | Ben-Haim et al. |
| 5,549,661 A | 8/1996 | Kordis et al. | 5,718,701 A | 2/1998 | Shai et al. |
| 5,553,612 A | 9/1996 | Lundbäck | 5,718,703 A | 2/1998 | Chin |
| 5,555,883 A | 9/1996 | Avitall | 5,720,775 A | 2/1998 | Lanard |
| 5,558,671 A | 9/1996 | Yates | 5,722,402 A | 3/1998 | Swanson et al. |
| 5,560,362 A | 10/1996 | Sliwa, Jr. et al. | 5,722,403 A | 3/1998 | McGee et al. |
| 5,562,699 A | 10/1996 | Heimberger et al. | 5,725,512 A | 3/1998 | Swartz et al. |
| 5,562,700 A | 10/1996 | Huitema et al. | 5,728,143 A | 3/1998 | Gough et al. |
| 5,562,720 A | 10/1996 | Stern et al. | 5,730,074 A | 3/1998 | Peter |
| 5,562,721 A | 10/1996 | Marchlinski et al. | 5,730,127 A | 3/1998 | Avitall |
| 5,564,440 A | 10/1996 | Swartz et al. | 5,730,704 A | 3/1998 | Avitall |
| 5,569,241 A | 10/1996 | Edwards | 5,730,757 A | 3/1998 | Benetti et al. |
| 5,571,088 A | 11/1996 | Lennox et al. | 5,733,280 A | 3/1998 | Avitall |
| 5,571,119 A | 11/1996 | Atala et al. | 5,735,280 A | 4/1998 | Sherman et al. |
| 5,571,215 A | 11/1996 | Sterman et al. | 5,735,290 A | 4/1998 | Sterman et al. |
| 5,573,532 A | 11/1996 | Chang et al. | 5,735,847 A | 4/1998 | Gough et al. |
| 5,575,766 A | 11/1996 | Swartz et al. | 5,735,849 A | 4/1998 | Baden et al. |
| 5,575,772 A | 11/1996 | Lennox | 5,738,628 A | 4/1998 | Sierocuk et al. |
| 5,575,788 A | 11/1996 | Baker et al. | 5,740,808 A | 4/1998 | Panescu et al. |
| 5,575,805 A | 11/1996 | Li | 5,755,664 A | 5/1998 | Rubenstein |
| 5,575,810 A | 11/1996 | Swanson et al. | 5,755,717 A | 5/1998 | Yates et al. |
| 5,578,007 A | 11/1996 | Imran | 5,755,760 A | 5/1998 | Maguire et al. |
| 5,582,609 A | 12/1996 | Swanson et al. | 5,759,158 A | 6/1998 | Swanson |
| 5,587,723 A | 12/1996 | Otake et al. | 5,769,846 A | 6/1998 | Edwards et al. |
| 5,588,432 A | 12/1996 | Crowley | 5,776,130 A | 7/1998 | Buysse et al. |
| 5,590,657 A | 1/1997 | Cain et al. | 5,782,827 A | 7/1998 | Gough et al. |
| 5,591,192 A | 1/1997 | Privitera et al. | 5,782,828 A | 7/1998 | Chen et al. |

| Patent No. | Date | Inventor(s) |
|---|---|---|
| 5,785,706 A | 7/1998 | Bednarek |
| H1745 H | 8/1998 | Paraschac |
| 5,788,636 A | 8/1998 | Curley |
| 5,792,140 A | 8/1998 | Tu et al. |
| 5,797,906 A | 8/1998 | Rhum et al. |
| 5,797,959 A | 8/1998 | Castro et al. |
| 5,797,960 A | 8/1998 | Stevens et al. |
| 5,800,428 A | 9/1998 | Nelson et al. |
| 5,800,482 A | 9/1998 | Pomeranz et al. |
| 5,800,484 A | 9/1998 | Gough et al. |
| 5,803,911 A | 9/1998 | Inukai et al. |
| 5,807,393 A | 9/1998 | Williamson et al. |
| 5,807,395 A | 9/1998 | Mulier et al. |
| 5,810,802 A | 9/1998 | Panescu et al. |
| 5,810,804 A | 9/1998 | Gough et al. |
| 5,810,805 A | 9/1998 | Sutcu et al. |
| 5,810,811 A | 9/1998 | Yates et al. |
| 5,814,028 A | 9/1998 | Swartz et al. |
| 5,817,005 A | 10/1998 | Cohen |
| 5,817,091 A | 10/1998 | Nardella et al. |
| 5,823,955 A | 10/1998 | Kuck et al. |
| 5,823,956 A | 10/1998 | Roth et al. |
| 5,827,216 A | 10/1998 | Igo et al. |
| 5,829,447 A | 11/1998 | Stevens et al. |
| 5,833,690 A | 11/1998 | Yates et al. |
| 5,833,703 A | 11/1998 | Manushakian |
| 5,836,311 A * | 11/1998 | Borst et al. ............... 128/897 |
| 5,836,947 A | 11/1998 | Fleischman et al. |
| 5,840,030 A | 11/1998 | Ferek-Petric et al. |
| 5,842,984 A | 12/1998 | Avitall |
| 5,843,075 A | 12/1998 | Taylor |
| 5,843,122 A | 12/1998 | Riza |
| 5,844,349 A | 12/1998 | Oakley et al. |
| 5,846,187 A | 12/1998 | Wells et al. |
| 5,846,191 A | 12/1998 | Wells et al. |
| 5,846,238 A | 12/1998 | Jackson et al. |
| 5,849,011 A | 12/1998 | Jones et al. |
| 5,849,020 A | 12/1998 | Long et al. |
| 5,849,028 A | 12/1998 | Chen |
| 5,853,411 A | 12/1998 | Whayne et al. |
| 5,855,590 A | 1/1999 | Malecki et al. |
| 5,855,614 A | 1/1999 | Stevens et al. |
| 5,860,975 A | 1/1999 | Goble et al. |
| 5,863,290 A | 1/1999 | Gough et al. |
| 5,863,291 A | 1/1999 | Schaer |
| 5,868,737 A | 2/1999 | Taylor et al. |
| 5,868,770 A | 2/1999 | Rygaard |
| 5,871,483 A | 2/1999 | Jackson et al. |
| 5,871,523 A | 2/1999 | Fleischman et al. |
| 5,871,525 A | 2/1999 | Edwards et al. |
| 5,873,845 A | 2/1999 | Cline et al. |
| 5,873,896 A | 2/1999 | Ideker |
| 5,875,782 A | 3/1999 | Ferrari et al. |
| 5,876,398 A | 3/1999 | Mulier et al. |
| 5,876,399 A | 3/1999 | Chia et al. |
| 5,876,400 A | 3/1999 | Songer |
| 5,876,401 A | 3/1999 | Schulze et al. |
| 5,879,295 A | 3/1999 | Li et al. |
| 5,879,296 A | 3/1999 | Ockuly et al. |
| 5,881,732 A | 3/1999 | Sung et al. |
| 5,882,346 A | 3/1999 | Pomeranz et al. |
| 5,885,278 A | 3/1999 | Fleischman |
| 5,891,028 A | 4/1999 | Lundbäck |
| 5,891,135 A | 4/1999 | Jackson et al. |
| 5,891,136 A | 4/1999 | McGee et al. |
| 5,891,138 A | 4/1999 | Tu et al. |
| 5,893,848 A | 4/1999 | Negus et al. |
| 5,893,863 A | 4/1999 | Yoon |
| 5,895,417 A | 4/1999 | Pomeranz et al. |
| 5,897,553 A | 4/1999 | Mulier |
| 5,897,554 A | 4/1999 | Chia et al. |
| 5,899,898 A | 5/1999 | Arless et al. |
| 5,899,899 A | 5/1999 | Arless et al. |
| 5,902,289 A | 5/1999 | Swartz et al. |
| 5,904,711 A | 5/1999 | Flom et al. |
| 5,906,580 A | 5/1999 | Kline-Schoder et al. |
| 5,906,587 A | 5/1999 | Zimmon |
| 5,906,606 A | 5/1999 | Chee et al. |
| 5,908,029 A | 6/1999 | Knudson et al. |
| 5,910,129 A | 6/1999 | Koblish et al. |
| 5,913,855 A | 6/1999 | Gough et al. |
| 5,913,876 A | 6/1999 | Taylor et al. |
| 5,916,213 A | 6/1999 | Haissaguerre et al. |
| 5,916,214 A | 6/1999 | Cosio et al. |
| 5,921,924 A | 7/1999 | Avitall |
| 5,921,982 A | 7/1999 | Lesh et al. |
| 5,924,424 A | 7/1999 | Stevens et al. |
| 5,925,038 A | 7/1999 | Panescu et al. |
| 5,925,042 A | 7/1999 | Gough et al. |
| 5,927,284 A | 7/1999 | Borst et al. |
| 5,928,138 A | 7/1999 | Knight et al. |
| 5,928,191 A | 7/1999 | Houser et al. |
| 5,928,229 A | 7/1999 | Gough et al. |
| 5,931,810 A | 8/1999 | Grabek |
| 5,931,836 A | 8/1999 | Hatta et al. |
| 5,931,848 A | 8/1999 | Saadat |
| 5,935,126 A | 8/1999 | Riza |
| 5,938,660 A | 8/1999 | Swarz et al. |
| 5,941,251 A | 8/1999 | Panescu et al. |
| 5,941,845 A | 8/1999 | Tu et al. |
| 5,944,718 A | 8/1999 | Austin et al. |
| 5,947,938 A | 9/1999 | Swartz et al. |
| 5,951,547 A | 9/1999 | Gough et al. |
| 5,951,552 A | 9/1999 | Long et al. |
| 5,954,661 A | 9/1999 | Greenspon et al. |
| 5,954,665 A | 9/1999 | Ben-Haim |
| 5,954,757 A | 9/1999 | Gray |
| 5,961,514 A | 10/1999 | Long et al. |
| 5,967,976 A | 10/1999 | Larsen |
| 5,971,980 A | 10/1999 | Sherman |
| 5,971,983 A | 10/1999 | Lesh |
| 5,972,013 A * | 10/1999 | Schmidt ............... 606/185 |
| 5,972,026 A | 10/1999 | Laufer et al. |
| 5,978,714 A | 11/1999 | Zadini et al. |
| 5,980,516 A | 11/1999 | Mulier et al. |
| 5,980,517 A | 11/1999 | Gough |
| 5,984,281 A | 11/1999 | Hacker et al. |
| 5,993,447 A | 11/1999 | Blewett et al. |
| 5,997,533 A | 12/1999 | Kuhns |
| 6,004,269 A | 12/1999 | Crowley et al. |
| 6,006,138 A | 12/1999 | Don Michael |
| 6,007,499 A | 12/1999 | Martin et al. |
| 6,010,516 A | 1/2000 | Hulka |
| 6,010,531 A | 1/2000 | Donlon et al. |
| 6,012,457 A | 1/2000 | Lesh |
| 6,013,074 A | 1/2000 | Taylor |
| 6,015,378 A | 1/2000 | Borst et al. |
| 6,016,809 A | 1/2000 | Mulier et al. |
| 6,016,811 A | 1/2000 | Knopp et al. |
| 6,017,358 A | 1/2000 | Yoon et al. |
| 6,023,638 A | 2/2000 | Swanson |
| 6,024,740 A | 2/2000 | Lesh et al. |
| 6,024,741 A | 2/2000 | Williamson et al. |
| 6,030,403 A | 2/2000 | Long et al. |
| 6,033,402 A | 3/2000 | Tu et al. |
| 6,036,641 A | 3/2000 | Taylor et al. |
| 6,036,670 A | 3/2000 | Wijeratne et al. |
| 6,039,731 A | 3/2000 | Taylor et al. |
| 6,039,733 A | 3/2000 | Buysse et al. |
| 6,039,748 A | 3/2000 | Savage et al. |
| 6,042,556 A | 3/2000 | Beach et al. |
| 6,047,218 A | 4/2000 | Whayne et al. |
| 6,048,329 A | 4/2000 | Thompson et al. |
| 6,050,996 A | 4/2000 | Schmaltz et al. |
| 6,059,719 A | 5/2000 | Yamamoto et al. |
| 6,060,454 A | 5/2000 | Duhaylongsod |

| | | | |
|---|---|---|---|
| 6,063,081 A | 5/2000 | Mulier | |
| 6,064,901 A | 5/2000 | Cartmell et al. | |
| 6,064,902 A | 5/2000 | Haissaguerre et al. | |
| 6,068,653 A | 5/2000 | LaFontaine | |
| 6,071,279 A | 6/2000 | Whayne et al. | |
| 6,071,281 A | 6/2000 | Burnside et al. | |
| 6,080,175 A | 6/2000 | Hogendijk | |
| 6,083,150 A | 7/2000 | Aznoian et al. | |
| 6,083,222 A | 7/2000 | Klein et al. | |
| 6,088,894 A | 7/2000 | Oakley | |
| 6,096,037 A | 8/2000 | Mulier | |
| 6,102,853 A | 8/2000 | Scirica et al. | |
| 6,110,098 A | 8/2000 | Renirie et al. | |
| 6,113,592 A | 9/2000 | Taylor | |
| 6,113,595 A | 9/2000 | Muntermann | |
| 6,113,598 A | 9/2000 | Baker | |
| 6,117,101 A | 9/2000 | Diederich et al. | |
| 6,120,496 A | 9/2000 | Whayne et al. | |
| 6,123,703 A | 9/2000 | Tu et al. | |
| 6,126,658 A | 10/2000 | Baker | |
| 6,129,662 A | 10/2000 | Li et al. | |
| 6,142,993 A | 11/2000 | Whayne et al. | |
| 6,142,994 A | 11/2000 | Swanson et al. | |
| 6,152,920 A | 11/2000 | Thompson et al. | |
| 6,156,009 A | 12/2000 | Grabek | |
| 6,156,033 A | 12/2000 | Tu et al. | |
| 6,161,543 A | 12/2000 | Cox et al. | |
| 6,162,195 A * | 12/2000 | Igo et al. | 604/164.13 |
| 6,162,220 A | 12/2000 | Nezhat | |
| 6,165,174 A | 12/2000 | Jacobs et al. | |
| 6,185,356 B1 | 2/2001 | Parker et al. | |
| 6,193,713 B1 | 2/2001 | Geistert et al. | |
| 6,199,556 B1 | 3/2001 | Benetti et al. | |
| 6,203,557 B1 | 3/2001 | Chin | |
| 6,206,823 B1 | 3/2001 | Kolata et al. | |
| 6,217,528 B1 | 4/2001 | Koblish et al. | |
| 6,217,576 B1 | 4/2001 | Tu et al. | |
| 6,224,592 B1 * | 5/2001 | Eggers et al. | 606/32 |
| 6,231,518 B1 * | 5/2001 | Grabek et al. | 600/508 |
| 6,235,024 B1 | 5/2001 | Tu | |
| 6,237,605 B1 | 5/2001 | Vaska et al. | |
| 6,238,334 B1 | 5/2001 | Easterbrook, III et al. | |
| 6,238,347 B1 | 5/2001 | Nix et al. | |
| 6,238,393 B1 | 5/2001 | Mulier | |
| 6,245,061 B1 | 6/2001 | Panescu et al. | |
| 6,245,064 B1 | 6/2001 | Lesh et al. | |
| 6,245,065 B1 | 6/2001 | Panescu et al. | |
| 6,251,092 B1 | 6/2001 | Qin et al. | |
| 6,251,128 B1 | 6/2001 | Knopp et al. | |
| 6,254,525 B1 | 7/2001 | Reinhardt et al. | |
| 6,264,087 B1 | 7/2001 | Whitman | |
| 6,264,670 B1 | 7/2001 | Chin | |
| 6,267,761 B1 | 7/2001 | Ryan | |
| 6,270,471 B1 | 8/2001 | Hechel et al. | |
| 6,273,887 B1 | 8/2001 | Yamauchi et al. | |
| 6,277,117 B1 | 8/2001 | Tetzlaff et al. | |
| 6,292,678 B1 | 9/2001 | Hall et al. | |
| 6,293,943 B1 | 9/2001 | Panescu et al. | |
| 6,296,619 B1 | 10/2001 | Brisken et al. | |
| 6,296,640 B1 | 10/2001 | Wampler et al. | |
| 6,302,880 B1 | 10/2001 | Schaer | |
| 6,304,712 B1 | 10/2001 | Davis | |
| 6,308,091 B1 | 10/2001 | Avitall | |
| 6,311,692 B1 | 11/2001 | Vaska et al. | |
| 6,312,383 B1 | 11/2001 | Lizzi et al. | |
| 6,314,962 B1 | 11/2001 | Vaska et al. | |
| 6,314,963 B1 | 11/2001 | Vaska et al. | |
| 6,319,230 B1 | 11/2001 | Palasis et al. | |
| 6,319,231 B1 | 11/2001 | Andrulitis | |
| 6,325,797 B1 | 12/2001 | Stewart et al. | |
| 6,328,736 B1 | 12/2001 | Mulier | |
| 6,332,089 B1 | 12/2001 | Acker et al. | |
| 6,332,468 B1 | 12/2001 | Benetti | |
| 6,332,881 B1 | 12/2001 | Carner et al. | |
| 6,334,860 B1 | 1/2002 | Dorn | |
| 6,356,790 B1 | 3/2002 | Maguire et al. | |
| 6,358,248 B1 | 3/2002 | Mulier | |
| 6,358,249 B1 | 3/2002 | Chen et al. | |
| 6,361,531 B1 | 3/2002 | Hissong | |
| 6,363,279 B1 | 3/2002 | Ben-Haim et al. | |
| 6,364,876 B1 | 4/2002 | Erb et al. | |
| 6,368,275 B1 | 4/2002 | Sliwa et al. | |
| 6,371,955 B1 | 4/2002 | Fuimaono et al. | |
| 6,381,499 B1 | 4/2002 | Taylor et al. | |
| 6,383,151 B1 | 5/2002 | Diederich et al. | |
| 6,385,472 B1 | 5/2002 | Hall et al. | |
| 6,391,024 B1 | 5/2002 | Sun et al. | |
| 6,394,948 B1 | 5/2002 | Borst et al. | |
| 6,398,792 B1 | 6/2002 | O'Connor | |
| 6,409,722 B1 | 6/2002 | Hoey | |
| 6,413,254 B1 | 7/2002 | Hissong et al. | |
| 6,419,648 B1 | 7/2002 | Vitek et al. | |
| 6,423,051 B1 | 7/2002 | Kaplan et al. | |
| 6,425,867 B1 | 7/2002 | Vaezy et al. | |
| 6,428,180 B1 | 8/2002 | Karram et al. | |
| 6,429,217 B1 | 8/2002 | Puskas | |
| 6,430,426 B2 | 8/2002 | Avitall | |
| 6,440,130 B1 | 8/2002 | Mulier | |
| 6,443,952 B1 | 9/2002 | Mulier | |
| 6,443,970 B1 | 9/2002 | Schulze et al. | |
| 6,447,443 B1 | 9/2002 | Keogh et al. | |
| 6,447,507 B1 | 9/2002 | Bednarek et al. | |
| 6,461,314 B1 | 10/2002 | Pant et al. | |
| 6,461,956 B1 | 10/2002 | Hsuan | |
| 6,464,630 B1 | 10/2002 | Borst et al. | |
| 6,464,700 B1 | 10/2002 | Koblish et al. | |
| 6,471,697 B1 | 10/2002 | Lesh | |
| 6,471,698 B1 | 10/2002 | Edwards et al. | |
| 6,474,340 B1 | 11/2002 | Vaska et al. | |
| 6,475,216 B2 | 11/2002 | Mulier | |
| 6,477,396 B1 | 11/2002 | Mest et al. | |
| 6,478,728 B1 | 11/2002 | Wright | |
| 6,484,727 B1 | 11/2002 | Vaska et al. | |
| 6,487,441 B1 | 11/2002 | Swanson et al. | |
| 6,488,678 B2 | 12/2002 | Sherman | |
| 6,488,680 B1 | 12/2002 | Francischelli | |
| 6,502,575 B1 | 1/2003 | Jacobs et al. | |
| 6,504,985 B2 | 1/2003 | Parker et al. | |
| 6,506,189 B1 | 1/2003 | Rittman, III et al. | |
| 6,506,200 B1 | 1/2003 | Chin | |
| 6,514,250 B1 | 2/2003 | Jahns | |
| 6,517,536 B2 | 2/2003 | Hooven | |
| 6,527,767 B2 | 3/2003 | Wang et al. | |
| 6,532,338 B1 | 3/2003 | Nemoto | |
| 6,537,248 B2 | 3/2003 | Mulier | |
| 6,540,740 B2 | 4/2003 | Lehmann et al. | |
| 6,546,935 B2 | 4/2003 | Hooven | |
| 6,549,812 B1 | 4/2003 | Smits | |
| 6,551,338 B1 * | 4/2003 | Chiu et al. | 606/186 |
| 6,554,768 B1 | 4/2003 | Leonard | |
| 6,558,314 B1 | 5/2003 | Adelman et al. | |
| 6,558,382 B2 | 5/2003 | Jahns | |
| 5,697,536 C1 | 6/2003 | Eggers et al. | |
| 6,575,969 B1 | 6/2003 | Rittman, III et al. | |
| 6,584,360 B2 | 6/2003 | Francischelli | |
| 6,585,732 B2 | 7/2003 | Mulier | |
| 6,591,049 B2 | 7/2003 | Williams et al. | |
| 6,605,084 B2 | 8/2003 | Acker et al. | |
| 6,610,055 B1 | 8/2003 | Swanson et al. | |
| 6,610,060 B2 | 8/2003 | Mulier | |
| 6,613,048 B2 * | 9/2003 | Mulier et al. | 606/49 |
| 6,632,222 B1 | 10/2003 | Edwards et al. | |
| 6,641,604 B1 | 11/2003 | Adelman et al. | |
| 6,645,199 B1 | 11/2003 | Jenkins et al. | |
| 6,648,883 B2 | 11/2003 | Francischelli | |
| 6,651,672 B2 | 11/2003 | Roth | |

| | | |
|---|---|---|
| 6,656,175 B2 | 12/2003 | Francischelli |
| 6,663,627 B2 | 12/2003 | Francischelli |
| 6,666,844 B1 | 12/2003 | Igo et al. |
| 6,679,882 B1 | 1/2004 | Kornerup |
| 6,692,450 B1 | 2/2004 | Coleman |
| 6,699,240 B2 | 3/2004 | Francischelli |
| 6,702,811 B2 | 3/2004 | Stewart et al. |
| 6,706,038 B2 | 3/2004 | Francischelli |
| 6,706,039 B2 | 3/2004 | Mulier |
| 6,716,211 B2 | 4/2004 | Mulier |
| 6,736,810 B2 | 5/2004 | Hoey |
| 6,755,827 B2 | 6/2004 | Mulier |
| 6,764,487 B2 | 7/2004 | Mulier |
| 6,773,433 B2 | 8/2004 | Stewart et al. |
| 6,776,780 B2 | 8/2004 | Mulier |
| 6,807,968 B2 | 10/2004 | Francischelli |
| 6,827,715 B2 | 12/2004 | Francischelli |
| 6,837,848 B2 | 1/2005 | Bonner et al. |
| 6,849,073 B2 | 2/2005 | Hoey |
| 6,858,028 B2 | 2/2005 | Mulier |
| 6,887,238 B2 | 5/2005 | Jahns |
| 6,899,711 B2 | 5/2005 | Stewart et al. |
| 6,911,019 B2 | 6/2005 | Mulier |
| 6,916,318 B2 | 7/2005 | Francischelli |
| 6,918,908 B2 * | 7/2005 | Bonner et al. ............ 606/41 |
| 6,936,046 B2 | 8/2005 | Hissong |
| 6,949,097 B2 | 9/2005 | Stewart et al. |
| 6,949,098 B2 | 9/2005 | Mulier |
| 6,960,205 B2 | 11/2005 | Jahns |
| 6,962,589 B2 | 11/2005 | Mulier |
| 6,969,373 B2 * | 11/2005 | Schwartz et al. ....... 604/170.03 |
| 2001/0031961 A1 | 10/2001 | Hooven |
| 2001/0039419 A1 | 11/2001 | Francischelli et al. |
| 2002/0002329 A1 | 1/2002 | Avitall |
| 2002/0002372 A1 | 1/2002 | Jahns et al. |
| 2002/0009275 A1 | 1/2002 | Williams et al. |
| 2002/0019629 A1 | 2/2002 | Dietz et al. |
| 2002/0032440 A1 | 3/2002 | Hooven |
| 2002/0052602 A1 | 5/2002 | Wang et al. |
| 2002/0082595 A1 | 6/2002 | Langberg et al. |
| 2002/0091382 A1 | 7/2002 | Hooven |
| 2002/0091383 A1 | 7/2002 | Hooven |
| 2002/0091384 A1 | 7/2002 | Hooven |
| 2002/0095139 A1 | 7/2002 | Keogh et al. |
| 2002/0099364 A1 | 7/2002 | Lalonde |
| 2002/0103484 A1 | 8/2002 | Hooven |
| 2002/0107513 A1 | 8/2002 | Hooven |
| 2002/0107514 A1 | 8/2002 | Hooven |
| 2002/0115990 A1 | 8/2002 | Acker |
| 2002/0115993 A1 | 8/2002 | Hooven |
| 2002/0120263 A1 | 8/2002 | Brown |
| 2002/0120316 A1 | 8/2002 | Hooven |
| 2002/0128643 A1 | 9/2002 | Simpson et al. |
| 2002/0138109 A1 | 9/2002 | Keogh et al. |
| 2002/0183738 A1 | 12/2002 | Chee et al. |
| 2003/0004507 A1 | 1/2003 | Francischelli et al. |
| 2003/0009094 A1 | 1/2003 | Segner et al. |
| 2003/0018252 A1 | 1/2003 | Duchon et al. |
| 2003/0018329 A1 | 1/2003 | Hooven |
| 2003/0028187 A1 | 2/2003 | Vaska et al. |
| 2003/0032952 A1 | 2/2003 | Hooven |
| 2003/0045871 A1 | 3/2003 | Jain et al. |
| 2003/0045872 A1 | 3/2003 | Jacobs |
| 2003/0050557 A1 | 3/2003 | Susil et al. |
| 2003/0060822 A1 | 3/2003 | Schaer et al. |
| 2003/0069572 A1 | 4/2003 | Wellman et al. |
| 2003/0069577 A1 | 4/2003 | Vaska et al. |
| 2003/0073991 A1 | 4/2003 | Francischelli et al. |
| 2003/0078570 A1 | 4/2003 | Heiner et al. |
| 2003/0078574 A1 | 4/2003 | Hall et al. |
| 2003/0091547 A1 | 5/2003 | Edelberg et al. |
| 2003/0093104 A1 | 5/2003 | Bonner et al. |
| 2003/0097124 A1 | 5/2003 | Lehmann et al. |
| 2003/0100895 A1 | 5/2003 | Simpson et al. |
| 2003/0114844 A1 | 6/2003 | Ormsby et al. |
| 2003/0120268 A1 | 6/2003 | Bertolero et al. |
| 2003/0125726 A1 | 7/2003 | Maguire et al. |
| 2003/0125729 A1 | 7/2003 | Hooven |
| 2003/0125730 A1 | 7/2003 | Berube et al. |
| 2003/0130598 A1 | 7/2003 | Manning et al. |
| 2003/0135207 A1 | 7/2003 | Langberg et al. |
| 2003/0144656 A1 | 7/2003 | Ocel |
| 2003/0144657 A1 | 7/2003 | Bowe et al. |
| 2003/0158548 A1 | 8/2003 | Phan et al. |
| 2003/0171745 A1 | 9/2003 | Francischelli et al. |
| 2003/0178032 A1 | 9/2003 | Ingle et al. |
| 2003/0191462 A1 | 10/2003 | Jacobs |
| 2003/0216724 A1 | 11/2003 | Jahns |
| 2004/0015106 A1 | 1/2004 | Coleman |
| 2004/0015219 A1 | 1/2004 | Francischelli |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0138621 A1 | 7/2004 | Jahns |
| 2004/0138656 A1 | 7/2004 | Francischelli |
| 2004/0143260 A1 | 7/2004 | Francischelli |
| 2004/0186465 A1 | 9/2004 | Francischelli |
| 2004/0215183 A1 | 10/2004 | Hoey |
| 2004/0216748 A1 | 11/2004 | Chin |
| 2004/0220560 A1 | 11/2004 | Briscoe |
| 2004/0236322 A1 | 11/2004 | Mulier et al. |
| 2004/0249368 A1 | 12/2004 | Hooven |
| 2004/0267326 A1 | 12/2004 | Ocel |
| 2005/0010095 A1 | 1/2005 | Stewart et al. |
| 2005/0033280 A1 | 2/2005 | Francischelli |
| 2005/0090815 A1 | 4/2005 | Francischelli |
| 2005/0143729 A1 | 6/2005 | Francischelli et al. |
| 2005/0165392 A1 | 7/2005 | Francischelli |
| 2005/0203561 A1 | 9/2005 | Palmer et al. |
| 2005/0203562 A1 | 9/2005 | Palmer et al. |
| 2005/0209564 A1 | 9/2005 | Bonner et al. |
| 2005/0256522 A1 | 11/2005 | Francischelli et al. |
| 2005/0261673 A1 | 11/2005 | Bonner |
| 2005/0267454 A1 * | 12/2005 | Hissong et al. ............ 606/27 |
| 2006/0009756 A1 | 1/2006 | Francischelli |
| 2006/0009759 A1 | 1/2006 | Chrisitian |
| 2006/0041243 A1 | 2/2006 | Nayak |
| 2007/0049863 A1 | 3/2007 | Jahns et al. |

FOREIGN PATENT DOCUMENTS

| | | |
|---|---|---|
| EP | 0 765 639 | 4/1997 |
| WO | 92/05828 | 4/1992 |
| WO | 93/25267 | 12/1993 |
| WO | 97/10764 | 3/1997 |
| WO | 97/32525 | 9/1997 |
| WO | 98/17187 | 4/1998 |
| WO | 98/53750 | 12/1998 |
| WO | 99/02096 | 1/1999 |
| WO | 99/04696 | 2/1999 |
| WO | 99/12487 | 3/1999 |
| WO | 99/44519 | 9/1999 |
| WO | 99/56486 | 11/1999 |
| WO | 99/56644 | 11/1999 |
| WO | 99/56648 | 11/1999 |
| WO | 99/59486 | 11/1999 |
| WO | 00/21449 | 4/2000 |
| WO | 00/27310 | 5/2000 |
| WO | 00/27311 | 5/2000 |
| WO | 00/27312 | 5/2000 |
| WO | 00/27313 | 5/2000 |
| WO | 00/42931 | 7/2000 |
| WO | 00/42932 | 7/2000 |

| | | |
|---|---|---|
| WO | 00/42933 | 7/2000 |
| WO | 00/42934 | 7/2000 |
| WO | 00/67647 | 11/2000 |
| WO | 02/00278 A2 | 11/2000 |
| WO | 00/72912 | 12/2000 |
| WO | 00/74574 | 12/2000 |
| WO | 01/82812 | 11/2001 |
| WO | 01/82813 | 11/2001 |
| WO | 00/67647 | 1/2002 |
| WO | 02/00278 | 1/2002 |
| WO | 02/087454 | 11/2002 |
| WO | 02/102252 | 12/2002 |
| WO | 03/105706 | 12/2003 |
| WO | 2004/064646 | 8/2004 |
| WO | 2004/064647 | 8/2004 |
| WO | 2007/002227 | 1/2007 |
| WO | 2007/005297 | 1/2007 |

OTHER PUBLICATIONS

Berjano, et al., "Bipolar Electrosurgery with Long Electrodes for RF Coagulation of Atrial Tissue," Proceedings 19th International Conference—IEEE/EMBS Oct. 30-Nov. 2, 1997, Chicago, IL, USA, pp. 2528-2530.

Cheng, et al., "Radiofrequency and Cryoablation of Atrial Fibrillation in Patients Undergoing Valvular Operations," Annals of Thoracic Surgery, 1998:65:1666-1672.

Elvan, et al., "Radiofrequency Catheter Ablation of the Atria Reduces Inducibility and Duration of ATrial Fibrillation in Dogs," Circulation, 1995:91(8):2235-2244 (17 pages).

Inoue, et al., "Video Assisted Thoracoscopic and Cardioscopic Radiofrequency Maze Ablation," ASAIO Journal, 1997, pp. 334-337.

Kawaguchi, et al., "Factors Affecting Rhythm After the Maze Procedure for Atrial Fibrillation," Circulation, 1996 94(9 Supp):II139-42.

Kim, et al., "The Cox-Maze III Procedure for Atrial Fibrillation Associated with Rheumatic Mitral Valve Disease," Annals of Thoracic Surgery, 1999;68:779-804.

Robbins, et al., "Pulmonary Vein Stenosis After Catheter Ablation of Atrial Fibrillation," Circulation, 1998; 98:1769-1775.

Thomas, et al., "Mechanism, Localization and Cure of Atrial Arrhythmias Occurring After a New Intraoperative Endocardial Radiofrequency Ablation Procedure for Atrial Fibrillation," Journal of the American College of Cardiology, 2000, vol. 35, No. 2, pp. 442-450.

Non-final office action from U.S. Appl. No. 10/156,315, dated Dec. 14, 2007 (11 pages).

Written opinion from International application No. PCT/US2004/000597 dated May 8, 2004 (7 pages).

Written opinion from International application No. PCT/US2006/024189 dated Apr. 1, 2007 (4 pages).

Written opinion from International application No. PCT/US2006/024191 dated Nov. 1, 2007 (6 pages).

Chitwood, "Will C. Sealy, MD: The Father of Arrhythmia Surgery—The Story of the Fisherman with a Fast Pulse," Annals of Thoracic Surgery 58:1228-1239, 1994.

Gallagher et al., "Cryosurgical Ablation of Accessory Atrioventrical Connections: A Method for Correction of the Pre-excitation Syndrome," Circulation 55(3): 471-479, 1977.

Sealy, "Direct Surgical Treatment of Arrhythmias: The Last Frontier in Surgical Cardiology," Chest 75(5): 536-537, 1979.

Sealy, "The Evolution of the Surgical Methods for Interruption of Right Free Wall Kent Bundles," The Annals of Thoracic Surgery 36(1): 29-36, 1983.

Guiraudon et al., "Surgical Repair of Wolff-Parkinson-White Syndrome: A New Closed-Heart Techique," The Annals of Thoracic Surgery 37(1): 67-71, 1984.

Klein et al., "Surgical Correction of the Wolff-Parkinson-White Syndrome in the Closed Heart Using Cryosurgery: A Simplified Approach," JACC 3(2): 405-409, 1984.

Randall et al., "Local Epicardial Chemical Ablation of Vagal Input to Sino-Atrial and Atrioventricular Regions of the Canine Heart," Journal of the Autonomic Nervous System 11:145-159, 1984.

Guiraudon et al., "Surgical Ablation of Posterior Septal Accessory Pathways in the Wolfe-Parkinson-White Syndrome by a Closed Heart Technique," Journal Thoracic Cardiovascular Surgery 92:406-413, 1986.

Gallagher et al., "Surgical Treatment of Arrhythmias," The American Journal of Cardiology 61:27A-44A, 1988.

Mahomed et al., "Surgical Division of Wolff-Parkinson-White Pathways Utilizing the Closed-Heart Technique: A 2-Year Experience in 47 Patients," The Annals of Thoracic Surgery 45(5): 495-504, 1988.

Cox et al., Surgery for Atrial Fibrillation; Seminars in Thoracic and Cardiovascular Surgery, vol. 1, No. 1 (1989) pp. 67-73.

Bredikis and Bredikis; Surgery of Tachyarrhythmia: Intracardiac Closed Heart Cryoablation; PACE, vol. 13, pp. 1980-1984 (1990).

McCarthy et al., "Combined Treatment of Mitral Regurgitation and Atrial Fibrillation with Valvuloplasty and the Maze Procedure," The American Journal of Cardiology 71: 483-486, 1993.

Yamauchi et al. "Use of Intraoperative Mapping to Optimize Surgical Ablation of Atrial Flutter," The Annals of Thoracic Surgery 56: 337-342, 1993.

Graffigna et al., "Surgical Treatment of Wolff-Parkinson-White Syndrome: Epicardial Approach Without the Use of Cardiopulmonary Bypass," Journal of Cardiac Surgery 8: 108-116, 1993.

Siefert et al., "Radiofrequency Maze Ablation for Atrial Fibrillation," Circulation 90(4): I-594 (1994) (2 pages).

Surgical treatment of atrial fibrillation: a review; Europace (2004) 5, S20-S29.

Elvan et al., "Radiofrequency Catheter Ablation of the Atria Reduces Inducibility and Duration of Atrial Fibrillation in Dog," Circulation 91: 2235-2244, 1995.

Cox et al., "Modification of the Maze Procedure for Atrial Flutter and Atrial Fibrillation. I. Rational and Surgical Results," The Journal of Thoracic Cardiovascular Surgery 110: 473-484, 1995.

Cox, "The Maze III Procedure for Treatment of Atrial Fibrillation," Sabiston DC, ed Atlas of Cardiothoracic Surgery, Philadelphia: WB Saunders: 460-475, 1994.

Sueda et al., "Simple Left Atrial Procedure for Chronic Atrial Fibrillation Associated with Mitral Valve Disease," The Annals of Thoracic Surgery 62(6): 1796-1800, 1996.

Tsui et al., "Maze 3 for Atrial Fibrillation: Two Cuts Too Few?" PACE 17: 2163-2166, 1994.

Kosakai et al., "Cox Maze Procedure for Chronic Atrial Fibrillation Associated with Mitral Valve Disease," The Journal of Thoracic Cardiovascular Surgery 108: 1049-1055, 1994.

Cox et al., "The Surgical Treatment of Atrial Fibrillation, IV Surgical Technique," *J Thorac Cardiovasc Surg*, 1991: 101: 584-592.

Nardella, "Radio Frequency Energy and Impedance Feedback," SPIE vol. 1068, Catheter Based Sensing and Imaging Technology (1989), 42-48.

Avitall et. al., "A Thoracoscopic Approach to Ablate Atrial Fibrillation Via Linear Radiofrequency Lesion Generation on the Epicardium of Both Atria," PACE, 1996;19(Part II):626,#241 (2 pages).

Sie et al., "Radiofrequency Ablation of Atrial Fibrillation in Patients Undergoing Mitral Valve Surgery. First Experience," Circulation, Supplement I 84:1-675 (1996).

Sie et al., "Radiofrequency Ablation of Atrial Fibrillation in Patients Undergoing Valve Surgery," Circulation, Supplement I, 84:I-450-I-451 (1997).

Jais et al., "Catheter Ablation for Paroxysmal Atrial Fibrillation: High Success Rates with Ablation in the Left Atrium," Circulation, Supplement I, 94:I-675-I-676 (1996).

Cox, "Evolving Applications of the Maze Procedure for Atrial Fibrillation," Ann Thorac Surg, 1993;55:578-580.

Cox et al. "Five-Year Experience with the Maze Procedure for Atrial Fibrillation," Ann Thorac Surg, 1993; 56:814-824.

Avitall et al., "New Monitoring Criteria for Transmural Ablation of Atrial Tissues," Circulation, 1996;94(Supp 1):I-493, #2889 (3 pages).

Cox et al., "An 8 1/2 Year Clinical Experience with Surgery for Atrial Fibrillation," Annals of Surgery, vol. 224, No. 3, 267-275 (1996).

Haïssaguerre et al., "Radiofrequency Catheter Ablation for Paroxysmal Atrial Fibrillation in Humans: Elaboration of a procedure based on electrophysiological data," in *Nonpharmacological Management*

*of Atrial Fibrillation*, Ed. F.D. Murgatroyd & A. J. Camm, Futura Publishing Co., Inc., NY, pp. 257-279 (1997).

Haïssaguerre et al., "Right and Left Atrial Radiofrequency Catheter Therapy of Paroxysmal Atrial Fibrillation," Journal of Cardiovascular Electrophysiology, 1996;7(12):1132-1144.

Haïssaguerre et al., "Role of Catheter Ablation for Atrial Fibrillation," Current Opinion in Cardiology, 1997;12:18-23.

Kawaguchi et al., "Risks and Benefits of Combined Maze Procedure for Atrial Fibrillation Associated with Organic Heart Disease," JACC, 1996;28(4):985-990.

Cox, et al., "Perinodal cryosurgery for atrioventricular node reentry tachycardia in 23 patients," Journal of Thoracic and Cardiovascular Surgery, 99:3, 1990, pp. 440-450.

Cox, "Anatomic-Electrophysiologic Basis for the Surgical Treatment of Refractory Ischemic Ventricular Tachycardia," Annals of Surgery, 1983; 198:2;119-129.

Williams, et al., "Left atrial isolation," J Thorac Cardiovasc Surg; 1980; 80: 373-380.

Scheinman, "Catheter-based Techniques for Cure of Cardiac Arrhythmias," Advances in Cardiovascular Medicine, 3:1-8 (1996).

Sueda et al., "Efficacy of a Simple Left Atrial Procedure for Chronic Atrial Fibrillation in Mitral Valve Operations," Ann Thorac Surg, 1997;63:1070-1075.

\* cited by examiner

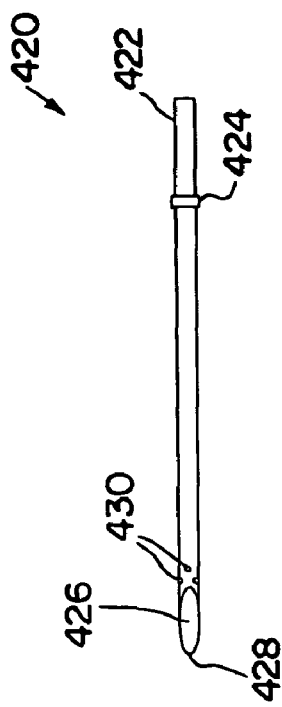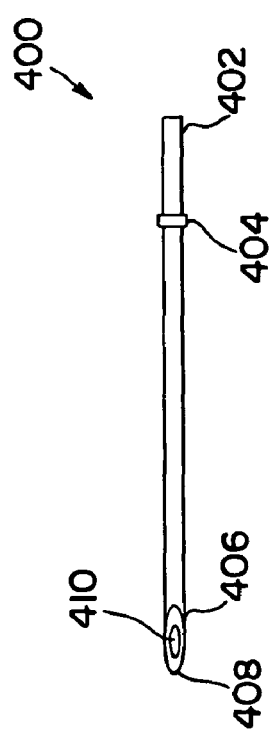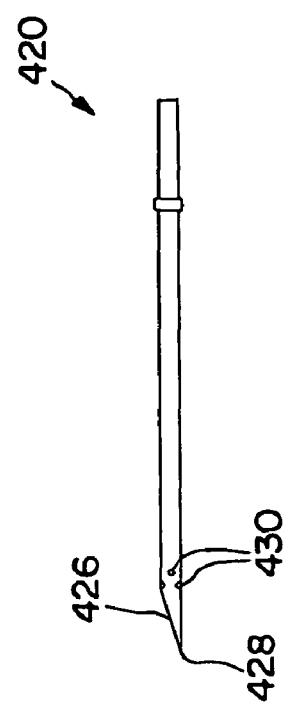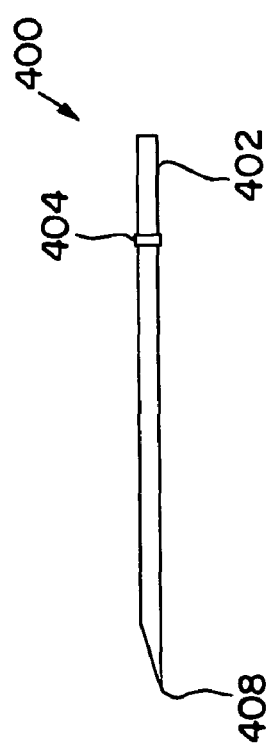

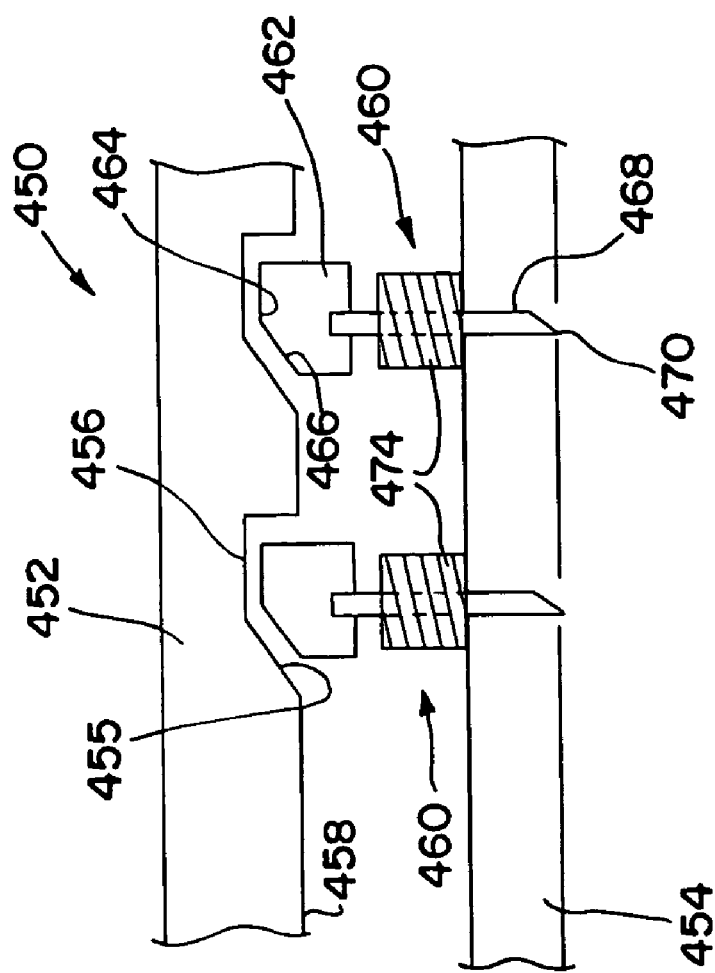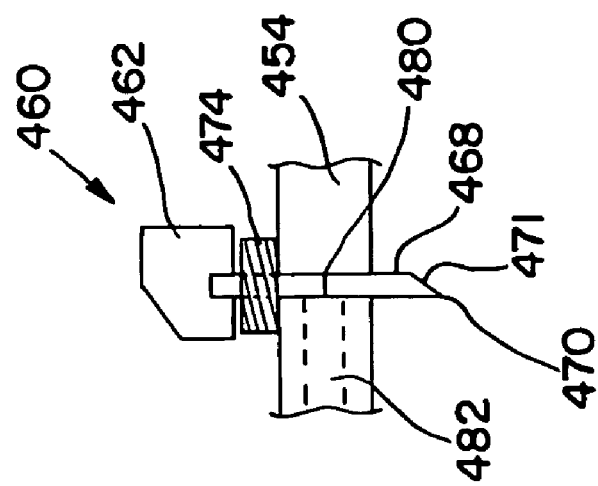

DEVICES AND METHODS FOR INTERSTITIAL INJECTION OF BIOLOGIC AGENTS INTO TISSUE

Cross-Reference To Related Applications

This application is a divisional of U.S. patent application Ser. No. 10/341,743, filed Jan. 14, 2003, now abandoned, the entire subject matter of which is incorporated herein by reference.

FIELD OF THE INVENTION

The present invention is related generally to medical devices and methods. More specifically, the present invention relates to methods and devices for injecting medical and biological agents into tissue. The present invention includes elongate devices having injection heads for transversely driving injection needles into tissue that find one, non-limiting use in a minimally invasive procedure for epicardially injecting cells into an infarct zone to repair myocardial tissue.

BACKGROUND OF THE INVENTION

Heart disease, including myocardial infarction, is a leading cause of death and impaired activity in human beings, particularly in the western world, most particularly among males. Heart disease can in turn degrade other physiological systems.

A stenosed or blocked coronary artery is one example of heart disease. A totally blocked, or substantially blocked coronary artery can cause immediate, intermediate term, and long-term problems. In the immediate term, myocardial cells can be starved of oxygen resulting in cell death. In the intermediate term, the cell death can "cascade", leading to cell death in adjacent cells. In the long term, the myocardial cell death, which creates weakened, non-contracting infarct regions of the heart, can lead to heart failure.

The immediate effects of a blocked coronary artery can be addressed through percutaneous coronary transluminal angioplasty (PCTA). PCTA can be used to dilate an occluded coronary artery, often in conjunction with stenting, to provide perfusing blood flow to cardiac cells downstream of the blockage. More intermediate term damage can be addressed through the systemic or local delivery of agents to reduce or treat the cells affected by the initial injury. The longer-term problems, for example, heart failure resulting from infarct cardiac tissue, can be addressed by the systemic or local delivery of medical agents to the cardiac tissue.

The direct delivery of agents to cardiac tissue is often preferred over the systemic delivery of such agents for several reasons. One reason is the substantial expense and small amount of the medical agents available, for example, agents used for gene therapy. Another reason is the substantially greater concentration of such agents that can be delivered directly into cardiac tissue, compared with the dilute concentrations possible through systemic delivery. Yet another reason is the undesirability or impossibility of systemically delivering agents to the heart tissue requiring treatment.

One mode of delivery for medical agents to myocardial tissue has been an epicardial, direct injection into myocardial tissue during an open chest procedure. Open chest procedures are inherently traumatic procedures with associated risks. The risks are often justified when the alternatives are a substantially high probability of death. In many cases, however, an open chest procedure is not believed justifiable only for the injection of medical agents into the myocardium.

Another approach taken to deliver medical agents into the myocardium has been an intravascular approach. Catheters may be advanced through the vasculature and into the heart to inject materials into myocardial tissue from within the heart. This approach may not allow all areas of the heart to be easily reached however. The size and type of instruments that can be advanced, for example, from a femoral artery approach, are also limited.

One relatively new therapy for treating infarcted cardiac tissue includes the injection of cells that are capable of maturing into actively contracting cardiac muscle cells. Examples of such cells include myocytes, mesenchymal stem cells, and pluripotent cells. Delivery of such cells into the myocardium is believed to be beneficial, particularly to prevent heart failure. Current intravascular delivery devices are less than optimal, being limited in the cardiac regions they can reach and the amount and types of materials they can deliver. Open chest procedures allow access to a larger range of cardiac tissue and also allow the delivery of greater varieties and amounts of agents, for example, cells. An open chest procedure may not be justifiable, however, only for the injection of such cells. In particular, patients having suffered a recent heart attack may be very poor candidates for such a procedure.

What would be desirable are improved devices that can be used to inject medical agents, for example, cells, into myocardial tissue without requiring an open chest procedure. In particular, devices enabling a minimally invasive cell delivery into myocardial tissue would be most advantageous.

SUMMARY OF THE INVENTION

The present invention provides a device for injecting medical agents into tissue, with a preferred medical agent being cells, for example, that can form contracting cardiac muscle cells. The device can be used to inject bone marrow cells, stem cells, pluripotent cells, and other cardiocyte precursor cells. The device can be used to inject these cells into infarct zones of cardiac tissue to prevent or postpone heart failure in heart disease patients. The devices and methods according to the present invention can be used to inject medical agents or substances into any soft tissue, including, but not limited to, heart, kidney, liver, tumor, and muscle tissue.

One device includes an elongate shaft having a distal region coupled to a plurality of hollow needles having sharp distal ends, with the needles operably coupled to the elongate shaft distal region such that the elongate shaft distal region is substantially perpendicular to the needle axes. The device can further include means for driving the needles along the needle axes in the direction of the needle sharp distal ends and means for discharging the fluid from the needle discharge ports. The device can further include a needle trigger operably coupled to the needle driving means for initiating the needle driving means and a discharge trigger operably coupled to the fluid discharge means for initiating fluid discharge from the needles. In one device, the means for driving the needles along the needle axes includes a first body having the needles fixedly attached thereto and a second body having the needles slidably disposed therethrough. In some devices, the first and second bodies each include a substantially planar portion substantially perpendicular to the needle axes. The means for driving the needles can include means for driving the first body toward the second body.

Some devices include a first body inclined portion disposed at an angle to the elongate shaft distal region longitudinal axis. The device can further include a third body longitudinally slidably coupled to the second body and being inclinably slidably coupled to the first body along the first body inclined portion. Longitudinally translating the third body relative to the second body can thus move the first body relative to the second body.

One device includes an elongate shaft having a distal region and an injection head coupled to the shaft distal region. The head can have a plurality of needles for injecting the substance into the tissue, where the needles are oriented substantially perpendicular to the elongate shaft distal region longitudinal axis. The device can include a needle driver for driving the plurality of needles past the injection head tissue-contacting surface and into the tissue. The device preferably includes means for transferring a longitudinal force directed along the shaft to a transverse force at the injection head. The means for transferring force can include two substantially planar members, where the first planar member has the plurality of needles fixedly and transversely attached thereto, and where the second planar member has the plurality of needles transversely and slidably disposed therethrough.

In some devices, the means for transferring force includes the first planar member being transversely slidably coupled to the second planar member, where the first planar member has at least one inclined portion disposed at an angle to the plane of the first planar member. A drive member can be slidably coupled to the second planar member to bear against the first planar member inclined portion. An elongate drive shaft can be slidably disposed along the elongate shaft and coupled to the drive member, such that moving the drive shaft longitudinally urges the drive member to bear against the inclined portion, urging the first planar member toward the second planar member and the plurality of needles away from the second planar member.

Another device includes a first and a second body coupled to each other through a pantograph mechanism having two opposing sides, where the pantograph includes a proximal arm pair and a distal arm pair on each side. The arm pairs can include a first member pivotally joined at one end to the first body, and a second member pivotally joined at one end to the second body. The first and second members each have second ends pivotally coupled to each other at a central joint, in a preferred embodiment. Moving the proximal and distal arm pair central joints closer together urges the first and second bodies apart, and moving the proximal and distal arm pair central joints closer together urges the first and second bodies together. In some devices, the central joint of each proximal and distal arm pair are joined to the corresponding joint on the opposite side, through a rod or other mechanism.

In still another device, the first body has a plurality of hollow needles attached thereto and a first plurality of magnets secured thereto. The second body has a plurality of needles slidably received therethrough. A third body can be slidably disposed on the second body and have a second plurality of magnets thereon, where the first and second plurality of magnets are disposed and have polarities oriented such that the slidable third body has a first position in which the first and third body are magnetically attracted to each other and a second position in which the first and third body are magnetically repulsed from each other. In this way, sliding the third member can pull the first body toward the second body and also push the first body away from the second body, depending on the degree of sliding. In one device, the third body has longitudinally adjacent magnetic pairs having opposite polarities, such that sliding the third member into the first position brings magnets having opposite facing polarities opposite each other, and sliding the third member into a second position brings magnets having the same facing polarities opposite each other.

In yet another device, the first body has a plurality of hollow needles attached thereto and a second body has the needles slidably received therethrough. The device can include a rack fixedly coupled to the second body and a pinion rotatably coupled to the first body and having teeth engaging the rack. Rotating the pinion in a first direction thus urges the first and second bodies closer together, and rotating the pinion in a second direction urges the first and second bodies further apart.

In another device, the first body has a plurality of hollow needles attached thereto and the second body has the plurality of needles slidably received therethrough. The first and second bodies can have a first expandable member disposed therebetween, such that expanding the first expandable member urges the first and second bodies apart and retracts the needles toward the second body. The expandable member can be a fluid inflatable member. In some devices, the first inflatable member is coupled to the first and second bodies and is deflatable, such that withdrawing fluid from the first inflatable member urges the first and second bodies closer together. Some devices further include a second expandable member disposed on the first body away from the second body and on a major surface facing away from the second body, such that disposing the second body against the tissue and disposing the second expandable member against a body part urges the first body toward the tissue.

In some devices, the plurality of needles attached to the first body may have a substantially different length as among the needles, to form a phased depth array of needles. The phased array of needles can distribute the initially higher force required to puncture the outer tissue temporally over the needle insertion process. In addition, the phased array of needles can allow the delivery one or more medical agents or substances at different depths within the tissue simultaneously.

DESCRIPTION OF THE DRAWINGS

FIGS. 15A and 15B illustrate a single orifice needle that can be used in conjunction with the distal injection heads;

FIGS. 16A and 16B illustrate another needle having eight side holes that can be used in conjunction with the distal injection heads;

FIG. 17 is a fragmentary, side view of needles that can be individually transversely driven by a cam mechanism;

FIG. 18 is a transverse, cross-sectional view of one cam driven needle of FIG. 17, having a side hole for admitting fluid into the needle;

DETAILED DESCRIPTION OF THE PREFERRED EMBODIMENTS

The following detailed description should be read with reference to the drawings, in which like elements in different drawings are numbered identically. The drawings, which are not necessarily to scale, depict selected embodiments and are not intended to limit the scope of the invention. Several forms of invention have been shown and described, and other forms will now be apparent to those skilled in art. It will be understood that embodiments shown in drawings and described below are merely for illustrative purposes, and are not intended to limit the scope of the invention as defined in the claims that follow.

Figure 1:
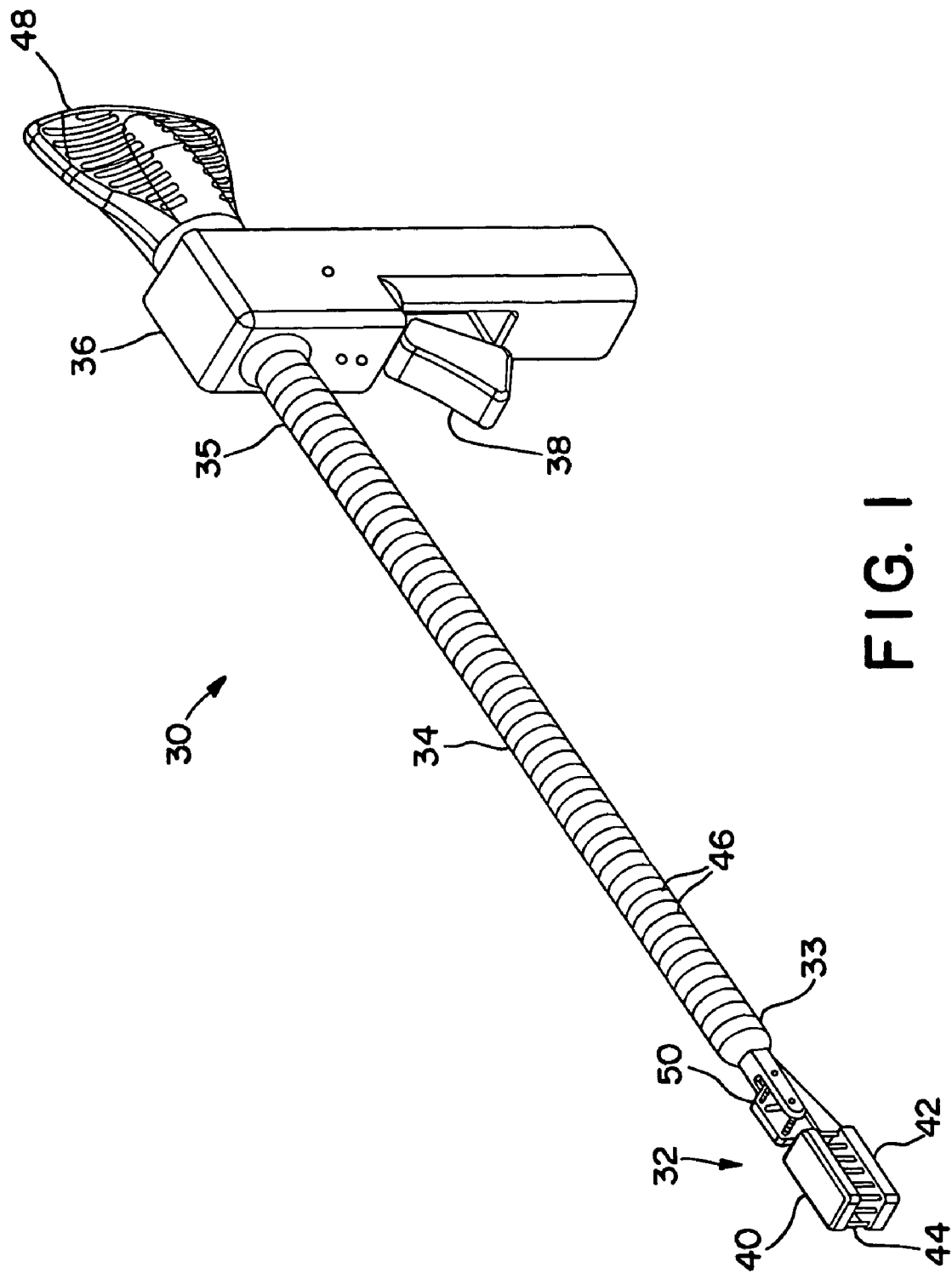
FIG. 1 is a perspective view of an interstitial injection device having a proximal handle, an elongate shaft, a distal injection head, and a mechanism for converting energy received through the elongate shaft to a transverse force to drive injecting needles from the distal injection head into tissue.
Figure 2:
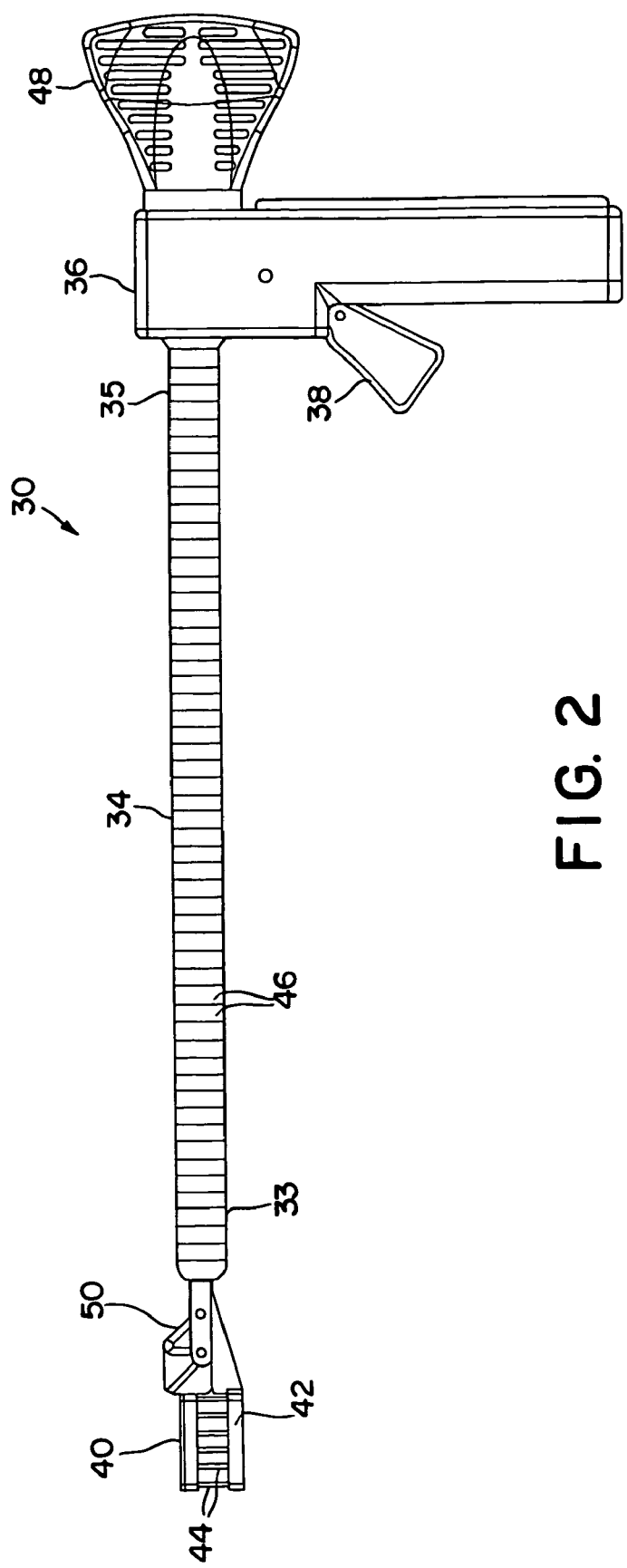
FIG. 2 is a side view of the interstitial injection device of FIG. 1.

FIGS. 1 and 2 illustrate an interstitial injection device 30 having a distal injection head 32, an elongate shaft 34, and a proximal handle 36. Elongate shaft 34 includes generally a distal region 33 and a proximal region 35. Proximal handle 36 includes a trigger mechanism 38 for initiating the needle insertion and/or fluid injection. Distal injection head 32 can include a first body 40, a second body 42, and numerous injecting needles 44. In a preferred embodiment, injecting needles 44 are fixedly attached to first body 40 and are slidably received through second body 42. Urging first body 40 towards second body 42 thus drives injecting needles 44 transversely through second body 42 and into the target tissue. Drawing first body 40 and second body 42 apart retracts injecting needles 44 from the tissue. In preferred embodiments, the depth of needle penetration can be controllably varied. In this way, the needle penetration depth can be varied to match the thickness of tissue, e.g., tissue of a heart chamber wall. In some embodiments, the first body is referred to as a "needle plate" and the second body is referred to as a "vacuum plate", as the second body can include vacuum suction pods for securing the device to tissue. Injection device 30 includes a mechanism 50 for translating energy that can be provided along elongate shaft 34 into transverse motion to urge needles 44 transversely into the tissue.

As used herein, with respect to the injection devices, the term "transversely" refers to a direction substantially orthogonal to a plane that includes the longitudinal axis of the elongate shaft distal portion. In the present application, a plane of injection may be defined as being orthogonal to the needles that are to extend into the tissue. Many embodiments of the invention include a needle driver that translates force parallel to the injection plane into a needle driving force. Thus, in many of the embodiments illustrated, the second body distal portion or vacuum plate extends substantially along or parallel to the injection plane. Similarly, as used in the present application, a surface may be defined as "inclined" with respect to the injection plane and may often be found to be inclined with respect to a plane extending through the second body distal portion or second body vacuum plate.

The elongate shaft provided can vary from embodiment to embodiment, with one ball-and-socket embodiment being illustrated in FIGS. 1 and 2. In this embodiment, several ball-and-socket elements 46 are nested within each other. Injection device 30 includes a proximal, rotable and threaded member 48 for increasing and decreasing tension on an elongate cable disposed through elongate shaft 34. Tightening rotable member 48 causes elongate shaft 34 to rigidly maintain its present position, while loosening rotable member 48 allows elongate member 34 to be formed into the desired shape. Other elongate handles are also within the scope of the present invention. Some elongate shafts include flexible elongate members that can be introduced using endoscopic methods through endoscopic device ports. Other elongate shafts are malleable shafts that can be bent into a desired shape that is then retained, absent a large application of further force. Some elongate shafts are flexible, and are introduced using endoscopes and other endoscopic instruments such as an endoscopic grasper or hemostat. Some flexible shafts have insufficient strength in compression to be advanced without being further stiffened with an enclosing guide tube or endoscope, or an enclosed stiffening stylet. Still other elongate shafts include pull wires for steering the shaft distal region from the proximal region. Pull wire technology is well known to those skilled in the art.

Figure 3:
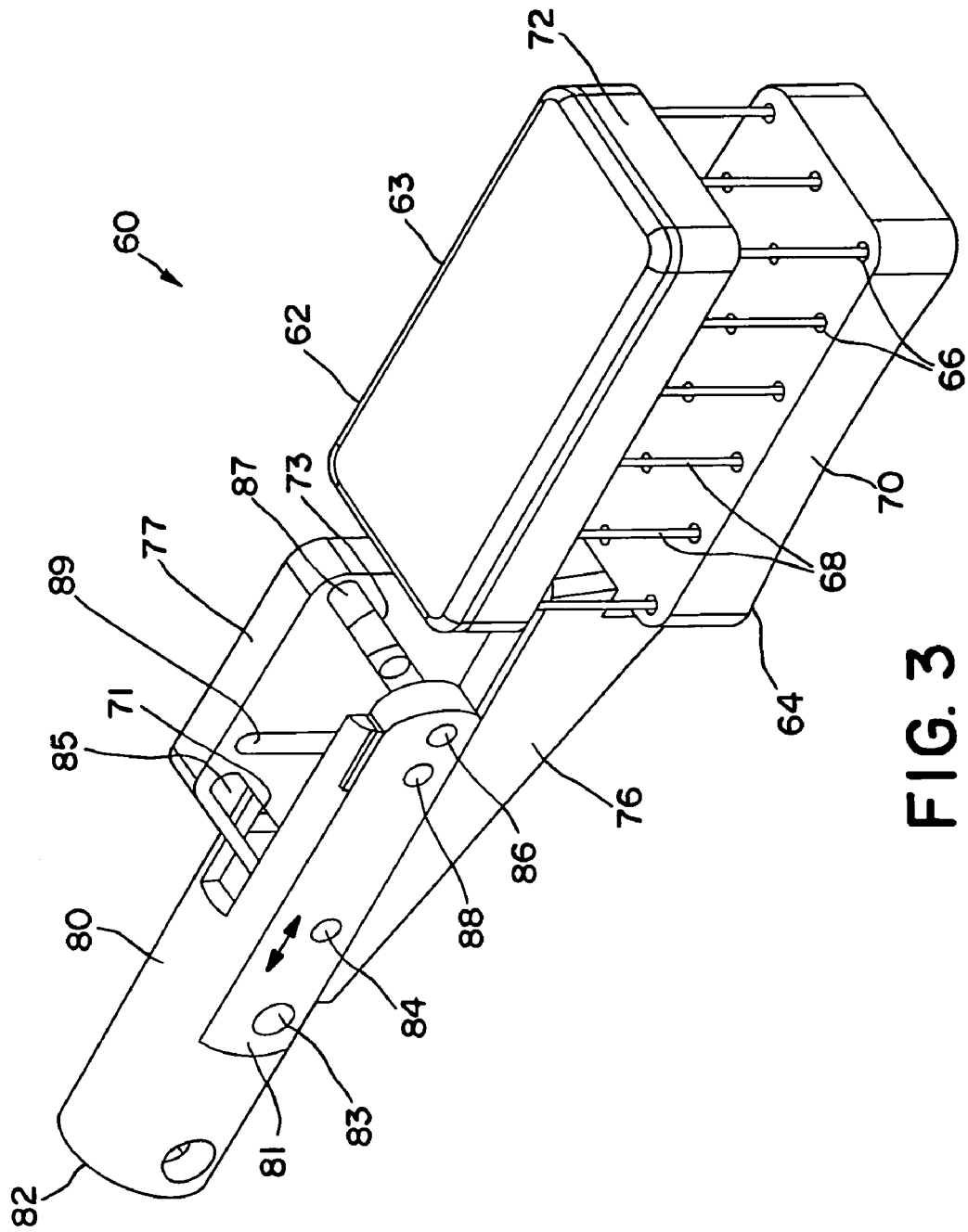
FIG. 3 is a perspective view of a distal injection head having a mechanism for translating a longitudinal motion to a transverse, needle driving motion through use of drive pins disposed through inclined slots.

FIG. 3 illustrates one example of a distal injection head 60 having a mechanical slide mechanism for translating longitudinal motion along the elongate shaft axis and perpendicular to the needles, to a transverse motion for driving needles into tissue. The mechanical slide mechanism may also be referred to as a cam mechanism. Mechanical slide distal injection head 60 includes generally a first body 62 and a second body 64, that can be maintained in a spaced-apart relationship to each other, and opened and closed through the mechanism described below. First body 62 includes numerous injecting needles 68 fixedly attached to first body 62. Needles 68 are slidably received through holes 66 in second body 64. First body 62 includes a distal portion 63 terminating in a distal end 72, and a proximal portion 77 that can slide transversely relative to second body 64. Injection head 60 further includes a drive member on yoke 81. Drive yoke 81 can slide longitudinally to drive first body 62 transversely.

Second body 64 includes a distal portion 70, an intermediate portion 76, and a proximal portion 80. Proximal portion 80 includes a proximal end 82 that can include a cavity for receiving part of the elongate shaft. Second body proximal portion 80 may also be referred to as a clevis. In some embodiments, second body 64 distal portion 70, intermediate portion 76, and proximal portion 80 are all rigidly joined together to move as a single piece. Injection head 60 further includes a drive yoke 81 longitudinally slidably disposed within second body proximal portion 80. Drive yoke 81 can include an internal blind cavity 83 to assist in coupling drive yoke 81 to a drive cable slidably disposed within an elongate shaft coupled to proximal end 82. Second body proximal portion 80 can be coupled to a rigid, outer sheath portion of the elongate shaft while drive yoke 81 is coupled to an elongate drive shaft or cable slidably disposed within the elongate shaft.

First body proximal portion 77 may be seen to include a proximal inclined drive slot 85, a distal inclined drive slot 87, and an intermediate guide slot 89 that is disposed transversely to the longitudinal axis of the elongate shaft coupled to first body proximal portion 80. Drive yoke 81 may be seen to include a proximal drive pin 84 slidably disposed within proximal inclined drive slot 85, an intermediate guide pin 88 extending through transverse guide slot 89, and a distal drive pin 86 extending through distal inclined drive slot 87. Inclined drive slots 85 and 87 may also be referred to as angled slots, having inclined or angled cam surfaces 71 and 73, respectively. Distal injection head 60 is shown in the open position, having drive yoke 81 in the proximal position and first body proximal portion 77 in the upward most position. Forcing a drive cable through the elongate shaft can force drive yoke 81 distally, causing pins 84 and 86 to bear against inclined surfaces 71 and 73 in inclined slots 85 and 87. This distal movement of pins 84 and 86 over inclined surfaces 71 and 73 urges first body proximal portion 77 downward, with slot 89 moving transversely downward over guide pin 88. As first body distal portion 63 is rigidly secured to first body proximal portion 77, first body distal portion 63 is urged toward second body distal portion 74, driving needles 68 through holes 66 and into the target tissue.

With the needles inserted into the tissue, agents can be injected into the tissue by the application of pressure through injection lumens (not shown in FIG. 3). First body distal portion 63 and second body distal portion 70 can be moved apart to retract the needles by proximally retracting drive yoke 81 to the position shown in FIG. 3.

Figure 4:
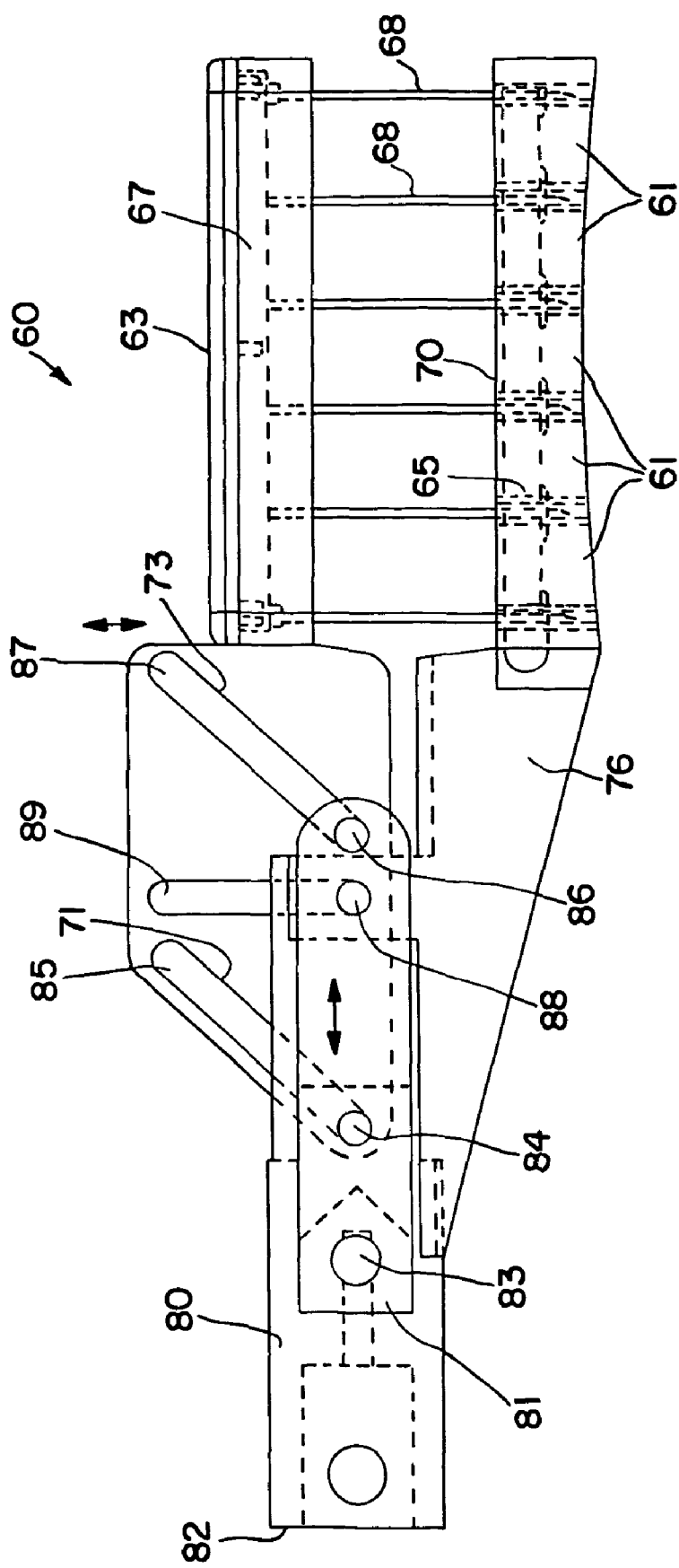
FIG. 4 is a side view of the injection head of FIG. 3.

FIG. 4 shows distal injection head 60 from the side. Second body distal portion 70 may be seen to include a vacuum lumen 65 coupled to several vacuum pods 61 that are in communication with vacuum lumen 65 and open at the bottom of second body distal portion 74. A vacuum line (not shown in FIG. 4) can be coupled to vacuum lumen 65 to reversibly adhere distal injection head 60 to the target tissue. In one example of use, distal injection head 60 can be urged against the epicardial surface of a heart, and vacuum applied to vacuum lumen 65 and vacuum pods 61 to adhere second body distal portion 70 to the heart. Vacuum pods are well known to those skilled in the art, and are currently provided on Medtronic products such as the Octopus® and Starfish®. A fluid manifold 67 may be seen coupled to needles 68 for supplying the needles with injectable material. Fluid manifold 67 can be coupled to a fluid supply tube or lumen extending along the length of the elongate shaft. In some embodiments, fluid manifold 67 serves as a reservoir, holding most or all of the material to be injected. Injection pressure can be provided by a fluid source coupled to the reservoir.

Figure 5:
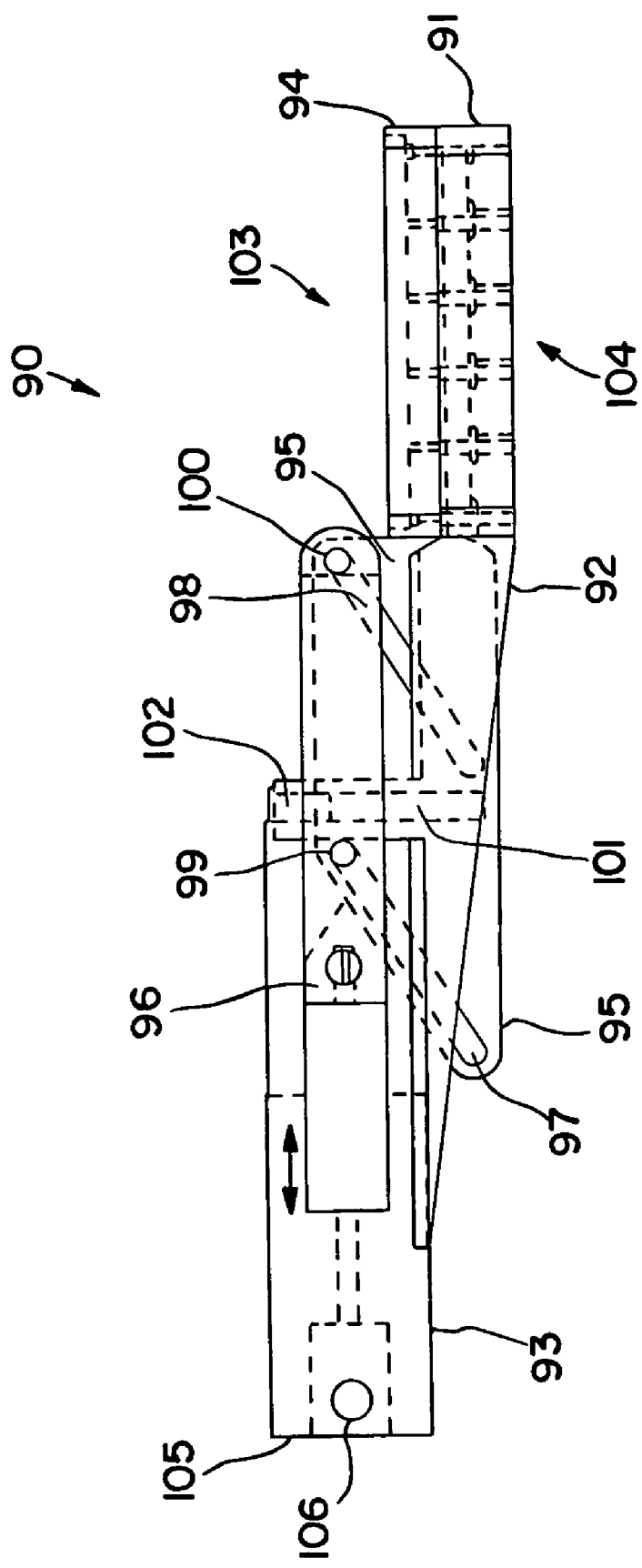
FIG. 5 is a side view of an injection head having a tongue-in-groove guide similar to that of FIGS. 3 and 4, shown in the closed, driving position.

FIG. 5 illustrates another mechanical slide mechanism for translating longitudinal movement along the elongate shaft to a transverse needle-driving movement at the injection head. Distal injection head 90 is similar in some respects to distal injection head 60 illustrated in FIGS. 3 and 4. Distal injection head 90 includes a proximal-most portion 105 for securing to an elongate shaft and a lumen 106 within for receiving a drive cable for attachment to a drive yoke 96. Distal injection head 90 includes generally a first body 103, and a second body 104 including several needles (not illustrated in FIG. 5) fixedly attached to first body 103 and slidably received through second body 104. First body 103 includes a distal portion or needle plate 94 secured to a proximal portion 95. First body proximal portion 95 includes inclined or angled drive slots 97 and 98 having inclined surfaces as described with respect to FIGS. 3 and 4. First body proximal portion 95 also has a groove guide 102 formed into each outward face, with only one face being illustrated in FIG. 5.

Distal injection head second body 104 includes a distal portion or vacuum plate 91 secured to an intermediate portion 92, which is in turn secured to a proximal portion 93. Second body vacuum plate 91, intermediate portion 92 and proximal portion 93, are all preferably rigidly secured to each other. Intermediate portion 92 preferably includes matching opposite portions on either side of first body proximal portion 95. Intermediate portion 92 includes a tongue 101 extending inwardly from each side of intermediate portion 92 into groove guides 102 in first body proximal portion 95. Tongue 101 is thus slidably and transversely received within groove 102. Intermediate portion 92 can form side-by-side jaws opposed to an inner jaw formed by first body proximal portion 95.

Drive yoke 96 may be seen slidably disposed within second body proximal portion 93. Drive yoke 96 includes drive pins 99 and 100 secured to drive yoke 96 and extending through inclined slots 97 and 98 of first body proximal portion 95, respectively. Drive yoke 96 is shown in the far, distal position, having forced drive pins 99 and 100 distally through inclined slots 97 and 98 to force first body proximal portion 95 downward to force needle plate 94 against vacuum plate 91. Second body intermediate portion 92 has had groove guide 102 of first body intermediate portion 95 slid downward over tongue 101 of second body intermediate portion 92. Proximally retracting drive yoke 96 relative to second body proximal portion 93 can force drive pins 99 and 100 to the far proximal ends of inclined slots 97 and 98, to force needle plate 94 away from vacuum plate 91.

Figure 6:
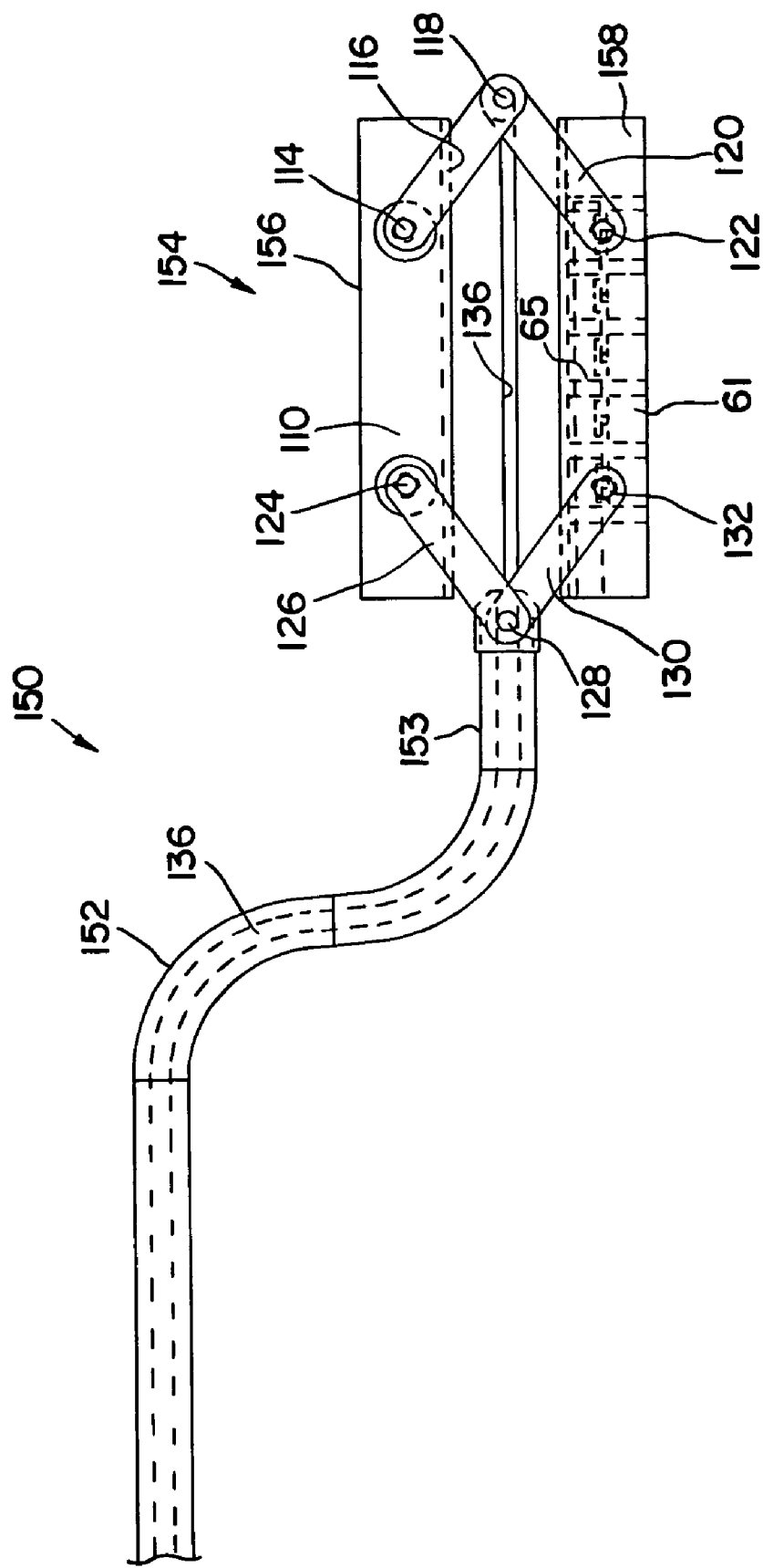
FIG. 6 is a side view of another distal injection head employing a four-link mechanism pantograph, attached to an elongate flexible sheath.

FIG. 6 illustrates an injection device 150 having an elongate, flexible sheath 152 and a distal injection head 154 utilizing a four-link pantograph mechanism. Flexible sheath 152 includes a distal portion 153 secured to distal injection head 154 and further includes a drive cable or rod 136 slidably disposed therethrough. Sheath 152 can also include a fluid injection lumen and a vacuum lumen within, or in separate tubes alongside.

Distal injection head 154 includes a first body 156 mounted in a spaced-apart relation to a second body 158. As previously described with respect to other embodiments, first body 156 can have several injecting needles fixedly attached to first body 156 and slidably received through holes in second body 158. Second body 158 may be seen to have vacuum pods 61 and a vacuum lumen 65, as previously described with respect to FIG. 3. First body 156 can have a fluid manifold within.

A first side 110 of distal injection head 154 is visible in FIG. 6, with a second, opposite side 112 (not visible in FIG. 6) located on the opposite side. Device 154 includes a distal arm pair including a first or upper distal arm 116 pivotally coupled to first body 156 at 114 and a second or lower arm 120 pivotally coupled to second body 158 at 122. First arm 116 is pivotally coupled to second arm 120 at a central distal joint 118. Device 154 also includes a proximal arm pair including a first or upper proximal arm 126 pivotally coupled to first body 158 at 124 and a second or lower arm 130 pivotally coupled to second body 158 at 132. First arm 126 is pivotally coupled to second arm 130 at a central proximal joint 128. Elongate, flexible sheath 152 includes drive cable or rod 136 slidably extending through sheath 152 and extending distally past proximal joint 128 to be coupled to distal joint 118. A corresponding set of four linkage arms may also be found on the opposite side of first body 156 and second body 158 (not visible in FIG. 6).

Inspection of FIG. 6 shows that distally extending drive cable or rod 136 acts to push proximal joint 128 and distal joint 118 further apart, thereby bringing first body 156 closer to second body 158, thereby urging the injecting needles through second body 158 and into the tissue. Similarly, retracting drive cable or rod 136 into flexible sheath 152 acts to bring proximal joint 128 and distal joint 118 closer together, thereby forcing first body 156 and second body 158 further apart, acting to retract the injecting needles.

In some embodiments, drive rod or cable 136 is externally helically threaded and is received through corresponding, receiving threads near distal joint 118 and/or proximal joint 128. In this embodiment, rotating drive cable or rod 136 can act to bring joints 128 and 118 either closer together or further apart, acting to advance needles into tissue or retract the needles from tissue, as previously described.

Figure 7:
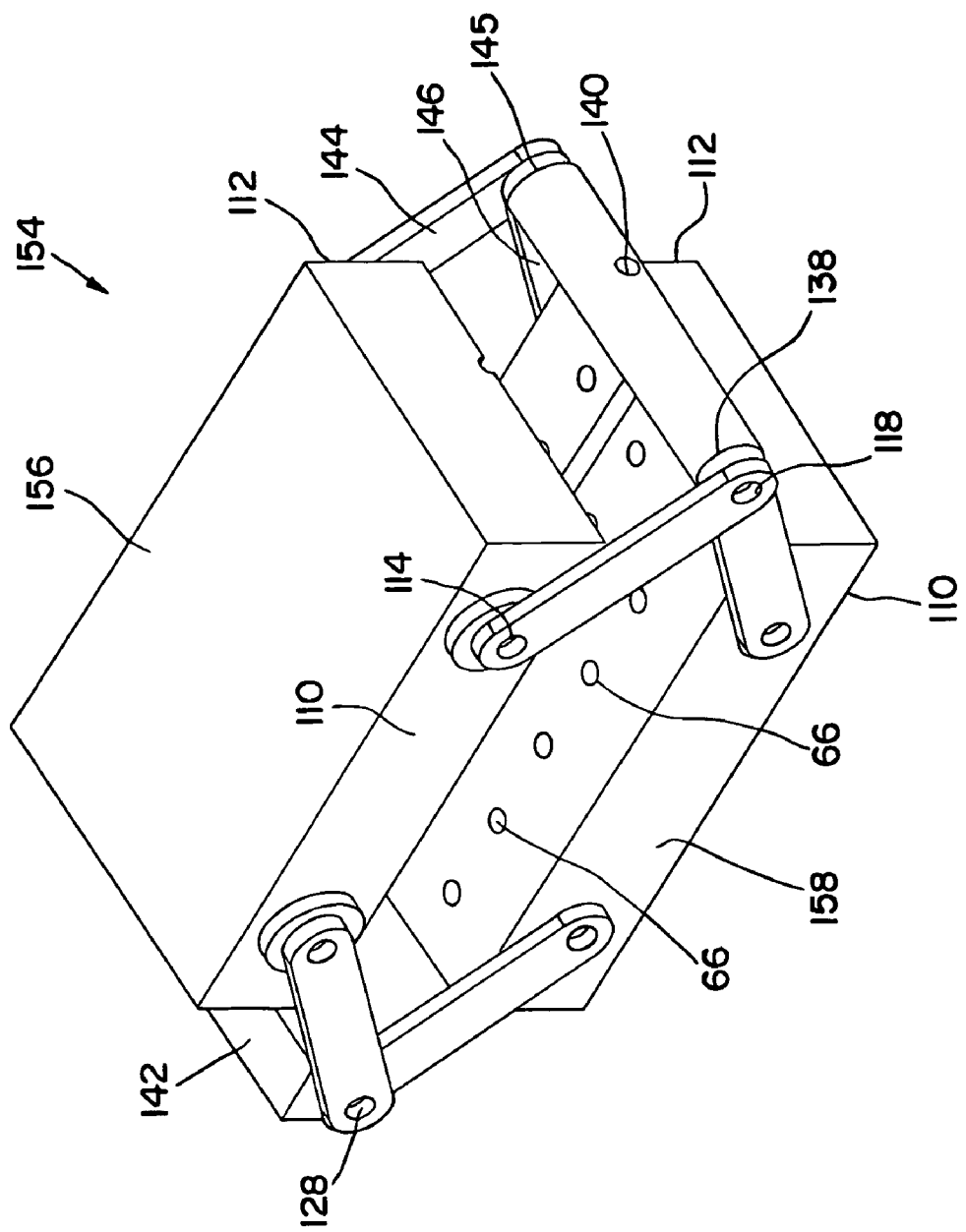
FIG. 7 is a perspective view of the distal injection head of FIG. 6.

FIG. 7 illustrates distal injection head 154 in greater detail. Distal central joint 118 may be seen to include a distal joint rod 138 that includes an aperture 140 for receiving drive cable or rod 136 therethrough. Proximal central joint 128 may also be seen to have a corresponding proximal joint rod 142. Distal injection head 154 also has a second, opposite side 112 carrying a second side, upper, distal linkage arm 144 and a second side, lower distal linkage arm 146, coupled to each other through distal, second side central joint 145. Joints such as 114 in first side 110 are coupled entirely through first body 156 to the second side 112 in some embodiments. In other embodiments, a rod or screw extends from joint 114 only partially into first body 156.

Figure 8:
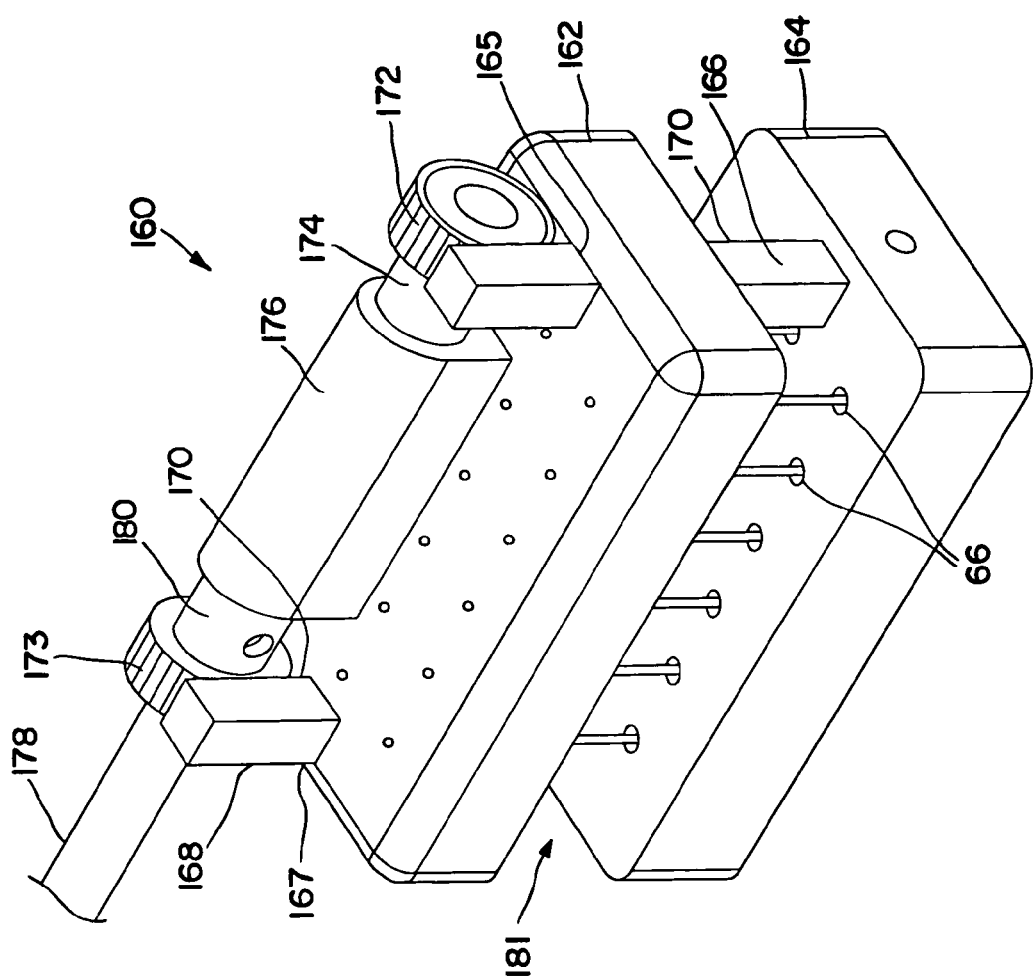
FIG. 8 is a fragmentary, perspective view of another distal injection head employing a rack and pinion mechanism.

FIG. 8 illustrates still another distal injection head 160, including a first body 162 slidably disposed in a spaced apart relationship to a second body 164. First body 162 has several needles forming a phased depth needle array 181 that is slidably disposed through holes 66 formed in second body 164. Phase needle array 181 is described below. Second body 164 has a distal guidepost 166 fixedly attached and slidably disposed through a distal opening 165 formed in first body 162. Similarly, second body 164 has a proximal guidepost 168 fixedly attached and slidably disposed through a proximal guide hole 167 in first body 162. Both distal guidepost 166 and proximal guidepost 168 carry a rack or set of teeth 170. A bushing 176 is fixedly attached to first body 162.

Distal injection head 160 further includes a rotable shaft 178 coupled to a proximal gear 185 including a tooth bearing portion 173 and a more distal bushing portion 180. Intermediate sleeve or bushing 176 has rotable shaft 178 rotatably disposed within. Shaft 178 continues distally to couple to a distal gear 187 including a proximal, bushing portion 174 and a tooth bearing portion 172. Teeth portions 173 and 172 engage teeth 170 on guideposts 166 and 168.

Inspection of FIG. 8 shows that rotating shaft 178 in a first direction will force first body 162 closer to second body 164, thereby driving needle array 181 into the target tissue. Similarly, rotating shaft 178 in the opposite direction will carry first body 162 away from second body 164, retracting the needle array.

Figure 9:
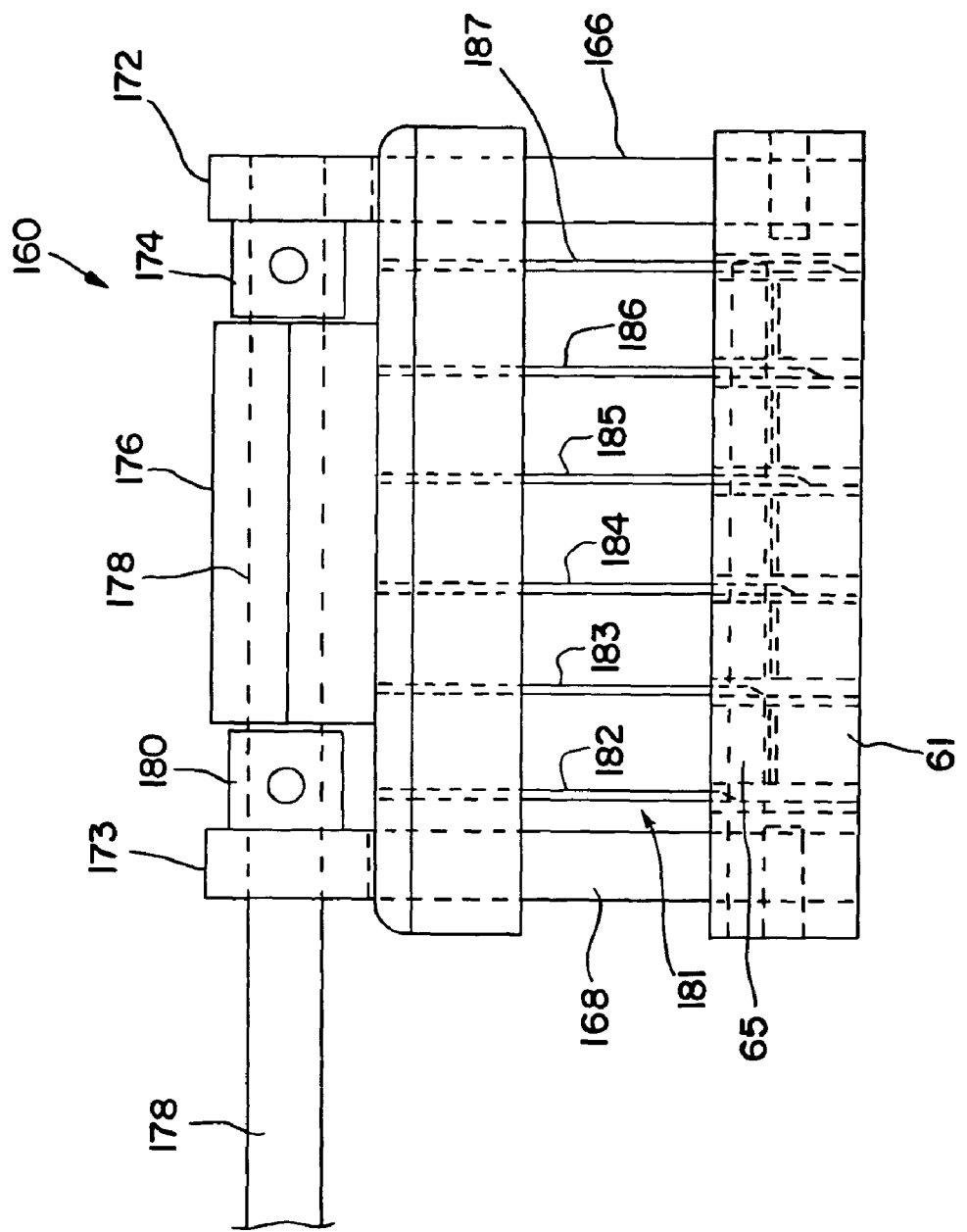
FIG. 9 is a fragmentary, side view of the distal injection head of FIG. 8, illustrating a phased array of needle depths.

FIG. 9 illustrates distal injection head 160, further showing vacuum pods 61 and vacuum lumen 65, as previously described with respect to other embodiments. Phased depth needle array 181 is illustrated in FIG. 9, including a series of needles, having varying lengths. In the example illustrated in FIG. 9, needles 182, 183, 184, 185, 186 and 187 each have a length greater than the previous, more proximal needle. This arrangement is for purposes of illustration only, with other arrangements, orders and depth pattern of needles all within the scope of the invention. Providing a phased depth array of needles allows tissue to be penetrated with less force. The force required to initially penetrate tissue, in particular, epicardial tissue, is generally greater than the force required to continually penetrate deeper into the tissue. The phased depth array of needles 181 provides an arrangement where this greater force requirement is felt first by needle 187, then 186, then 185, and so forth. This arrangement does not require that the initial, greater resistance encountered by a single needle penetrating outer tissue be encountered by all the needles at the same time. In addition, the phased needle array can allow the delivery of one or more medical agents or substances at different depths within the tissue simultaneously. The phased needle array may be used in any embodiment illustrated in the present application.

Figure 10:
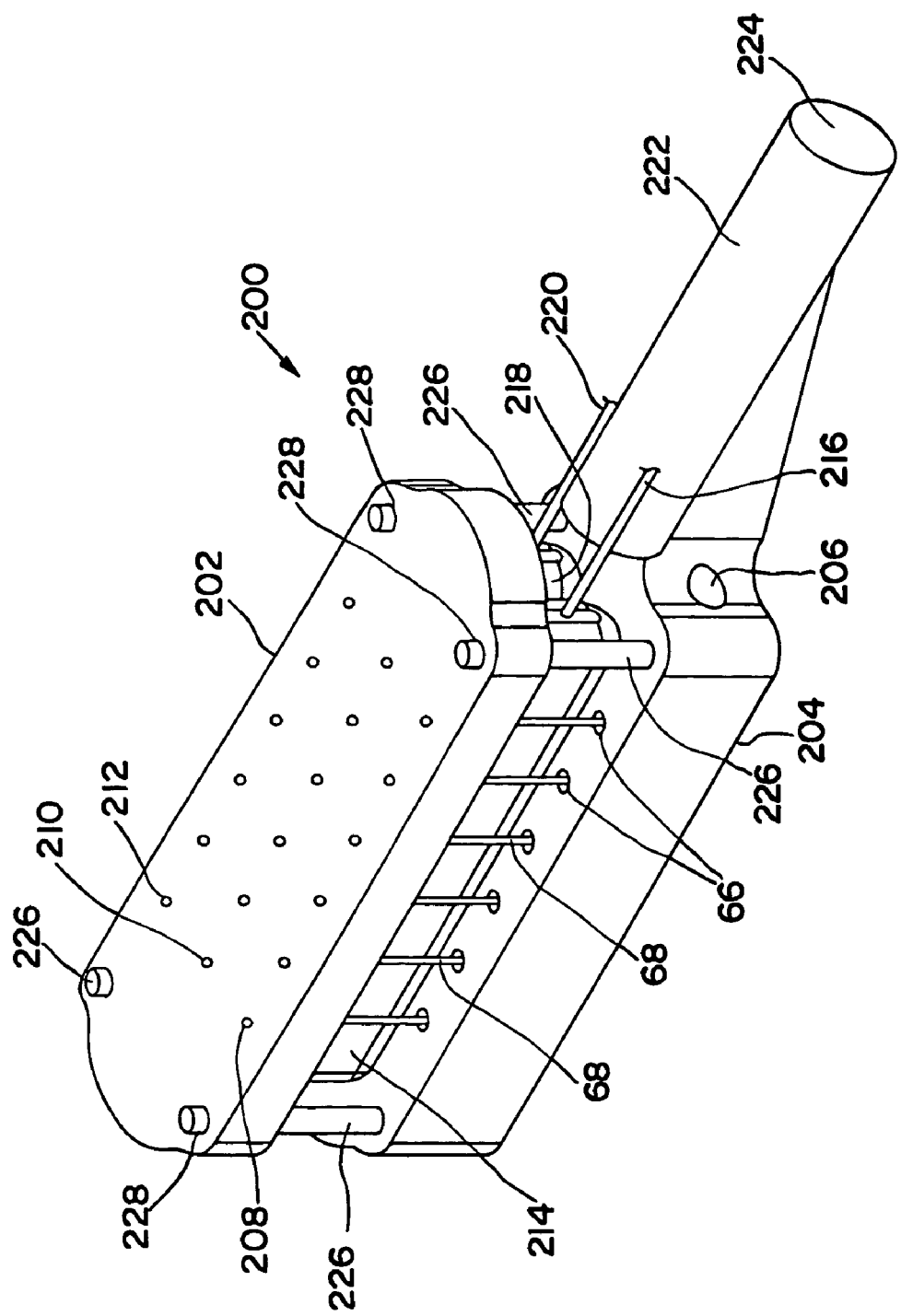
FIG. 10 is a perspective view of a distal injection head employing inflatable balloons to open and close the head.

FIG. 10 illustrates still another distal injection head 200, including a first body 202 and a second body 204. First body 202 can have a series of needles 68 fixedly attached, and oriented in a first longitudinal row 208, an intermediate longitudinal row 210, and an opposite side longitudinal row 212. A first inflatable and deflatable envelope, balloon, or bellows 214 may be seen disposed between needle rows 208 and 210. First inflatable envelope 214 can be coupled to an inflation and deflation tube 216. Similarly, a second inflation and deflation tube 220 may be seen supplying a second inflatable and deflatable envelope, balloon, or bellows 218 that is disposed between needle row 210 and 212.

Inflatable envelopes 214 and 218, and other inflatable envelopes in the present application can be cylindrical, round, or pancake shaped. The envelopes can be made of many polymeric materials, including polyurethane, latex, PVC, silicone, and polyamide. Distal inflation head 200 includes a proximal, mounting stub 222, including a proximal aperture 224. Distal injection head 200 further includes an aperture or port 206 that can be used for supplying vacuum to the vacuum pods, previously described. Inflation and deflation tubes 216 and 220 can continue along the length of the elongate shaft or be carried within the elongate shaft for much of its length, either as separate tubes or integral lumens, depending on the embodiment. Similarly, vacuum aperture or port 206 can be coupled along the length of the shaft through a separate vacuum tube or have the vacuum carried within a lumen within the elongate shaft itself. Second body 204 has four guideposts. 226 fixedly attached to second body 204. Guideposts 226 are slidably received within receiving apertures 228 formed in first body 202.

In use, distal injection head 200 can be advanced to the tissue site of interest, and disposed against the tissue. In some embodiments, a vacuum is applied through vacuum pods, as previously described. A vacuum can then be applied to envelopes 214 and 226, acting to pull first body 202 toward second body 204, and drive needles 68 through second body 204 and into the tissue.

Inflation pressure can be supplied through tubes 216 and 220 to envelopes 214 and 226, urging first body 202 away from second body 204, thereby retracting needles 68 from the tissue. In some embodiments, a gas, for example, carbon dioxide or nitrogen or air is injected through tubes 216 and 220 to inflate inflatable envelopes 214. In other embodiments, liquid, for example, saline, is supplied to tubes 216 and 220 to operate distal injection head 200. In some embodiments, the depth of needle penetration can be controllably and variably set by adjusting the inflation pressure.

Figure 11:
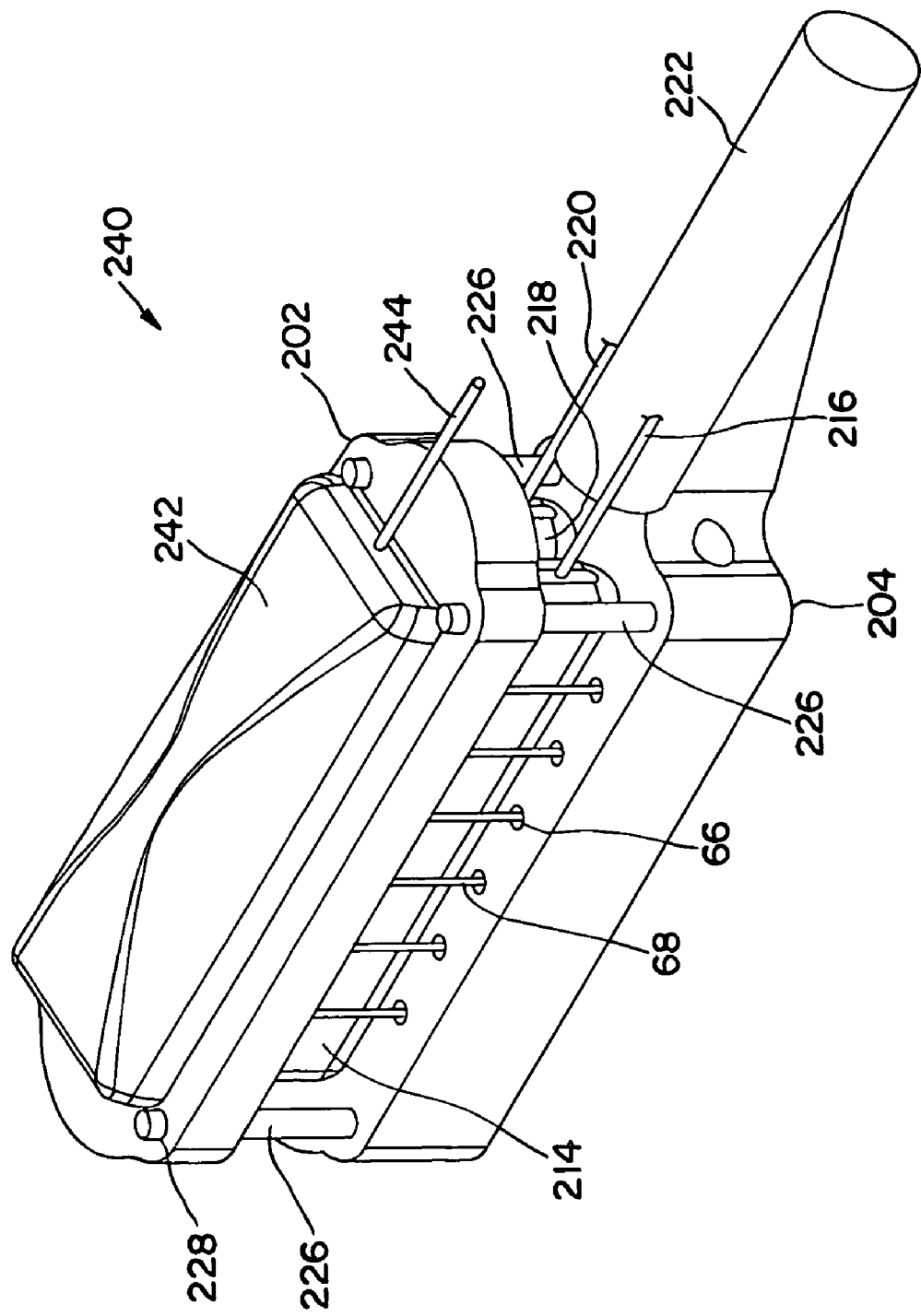
FIG. 11 is a perspective view of yet another distal injection head employing inflatable balloons for withdrawing needles and another inflatable balloon for transversely driving needles into tissue and/or stabilizing the head.

FIG. 11 illustrates another distal injection head 240, similar in many respects to injection head 200 illustrated in FIG. 10. Injection head 240 includes first body 202, second body 204, proximal hub 222, needles 68, needle receiving holes 66, first inflatable envelope 214, second inflatable envelope 218 and guide posts 226, all as previously described with respect to injection device 200 of FIG. 10. Distal injection device 240 further includes another inflatable envelope, balloon, or bellows 242 fixedly attached to the top of first body 202 and supplied by another inflation and deflation tube 244. Inflatable envelope 242 is thus located on the body opposite the body disposed against the tissue, and on the opposite side or major surface of that body. Inflatable envelope 242 may be used to force distal injection head 240 against the target tissue. In one use, inflatable envelope 242 is inflated to fill the pericardial space and press against the inside of the pericardial sac to stabilize the position of distal injection head 240 against the epicardial surface. In some methods, inflatable envelope 242 is used in conjunction with vacuum pods to stabilize the position of the distal injection head against the epicardial surface. In other methods, inflatable envelope 242 is used to replace the vacuum pods. In still other methods, inflatable envelope 242 is used to provide some or all of the transverse driving force to drive needles 68 into the target tissue.

Figure 12:
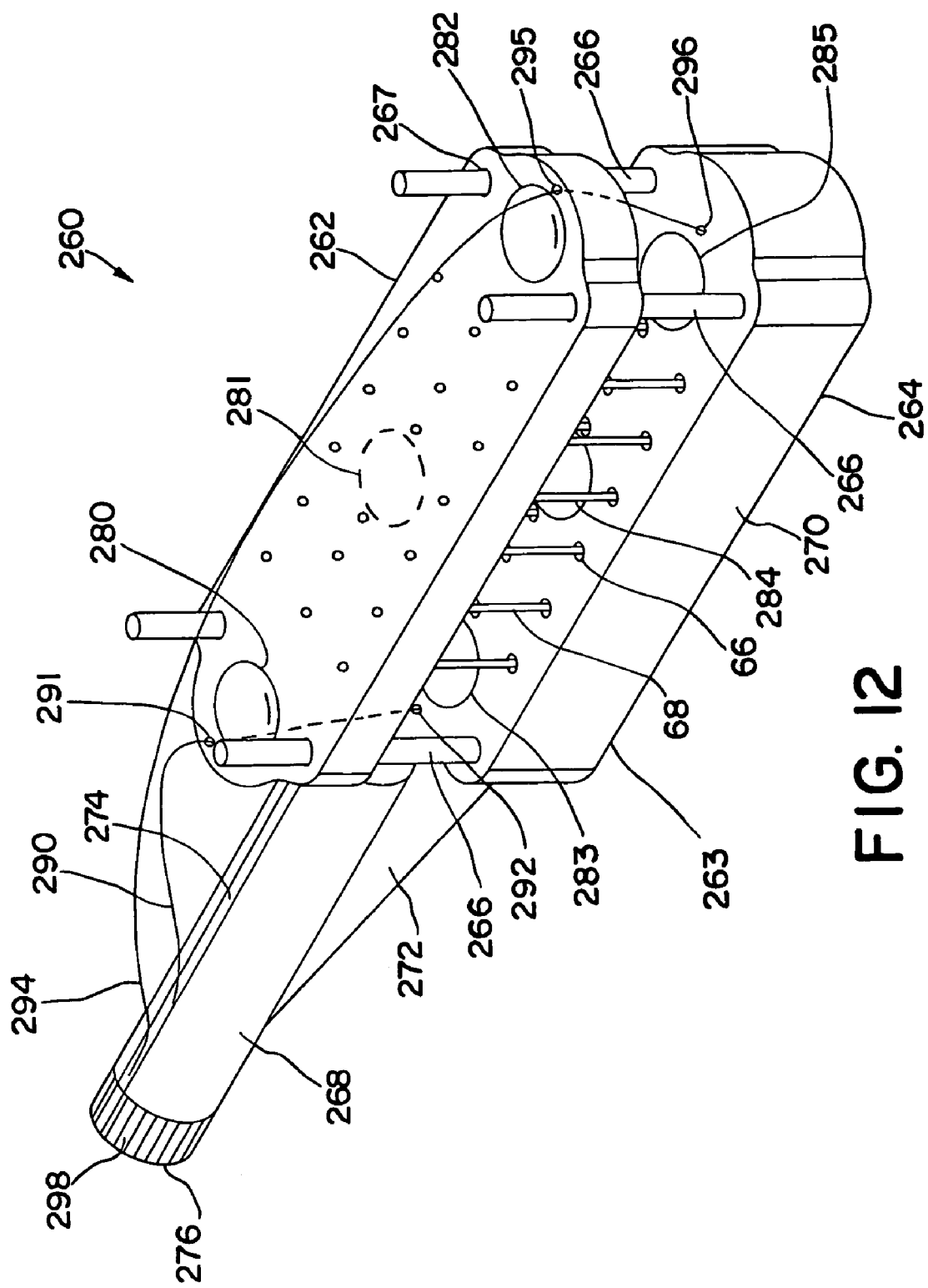
FIG. 12 is a perspective view of still another distal injection head employing drawstrings to drive needles into tissue and magnets to bias the needles away from the tissue.

FIG. 12 illustrates another distal injection head 260 including a first body 262 and a second body 263. Second body 263 includes a distal portion 264 that can serve as a vacuum plate in some embodiments, an intermediate portion 272 that can act as a strut or brace, and a proximal portion 268 for coupling to an elongate shaft. Second body proximal portion 268 may be seen to include a longitudinal slit 274 along its length and terminate proximately in a proximal aperture or port 276. Second body 263 has attached guideposts 266 that are slidably received within guide holes 267 in first body 262.

First body 262 may be seen to include three magnets 280, 281, and 282. Second body distal portion 270 also includes three magnets 283, 284, and 285. The magnets may be oriented such that each of the opposing pairs of magnets repel each other. Thus, magnet 280 may have the positive pole oriented downward and corresponding second body magnet 283 may have the positive pole oriented upward, and so forth. The pairs formed by magnets 280 and 283, 281 and 284, and 282 and 285 can act to magnetically bias first body 262 away from second body 264. This magnetic repulsive force may be used in conjunction with other embodiments described elsewhere in the present application.

Distal injection head 260 may also be seen to include a first drawstring or wire 290 extending outward from slot 274, extending through a receiving hole 291 in first body 262, and terminating at a hole or junction point 292 in second body distal portion 264. Similarly, a second pullstring, wire, or tether 294 may be seen also extending from slot 274, extending through a distal receiving hole 295 in first body 264 and terminating in a receiving hole or connection point 296 in second body distal portion 264. A proximal collar 298 may be seen disposed about longitudinal slot 274, limiting the transverse travel of tethers 294 and 290 from longitudinal slot 274.

In use, tethers 290 and 294 may be proximally retracted through longitudinal slot 274 and collar 298. As tethers 290 and 294 are slidably received through holes 291 and 295, respectively, retracting the tethers acts to force first body 262 toward second body distal portion 264. This acts to drive needles 68 through receiving holes 66 and into the target tissue. When the tethers are relaxed, the biasing force of the magnet pairs acts to retract the needles from the target tissue. In some embodiments, electromagnets are used in place of some or all of the magnets, with the wires or electrodes extending the length of the elongate shaft to provide energy to the electromagnets. In the electromagnetic embodiments, the polarity of the magnets can be reversed electronically, to both extend the needles and retract the needles.

Figure 13:
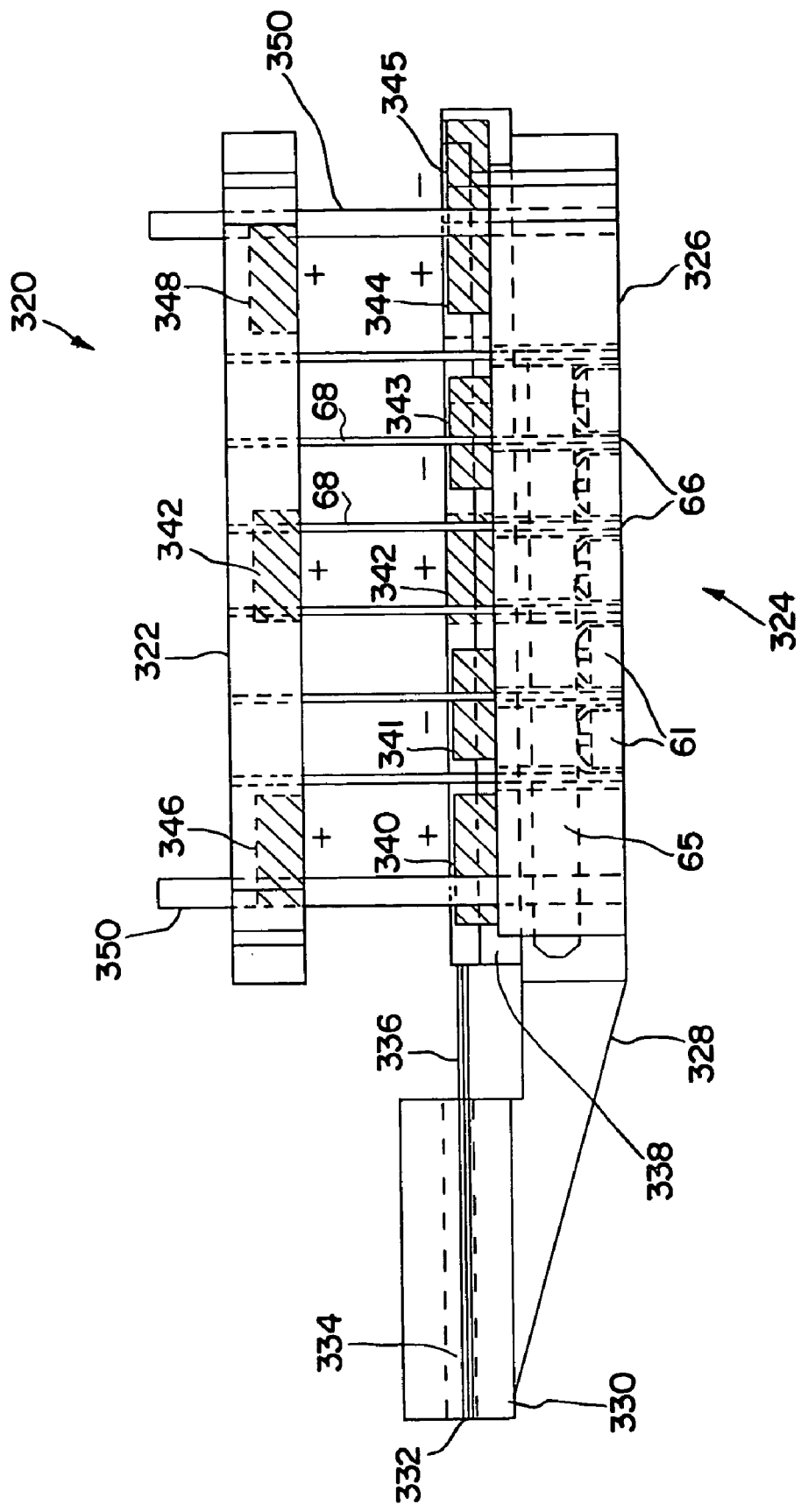
FIG. 13 is a side view of another distal injection device employing alternating polarity magnet pairs slideably disposed opposite other magnets to translate longitudinal motion into transverse, needle-driving motion.
Figure 14:
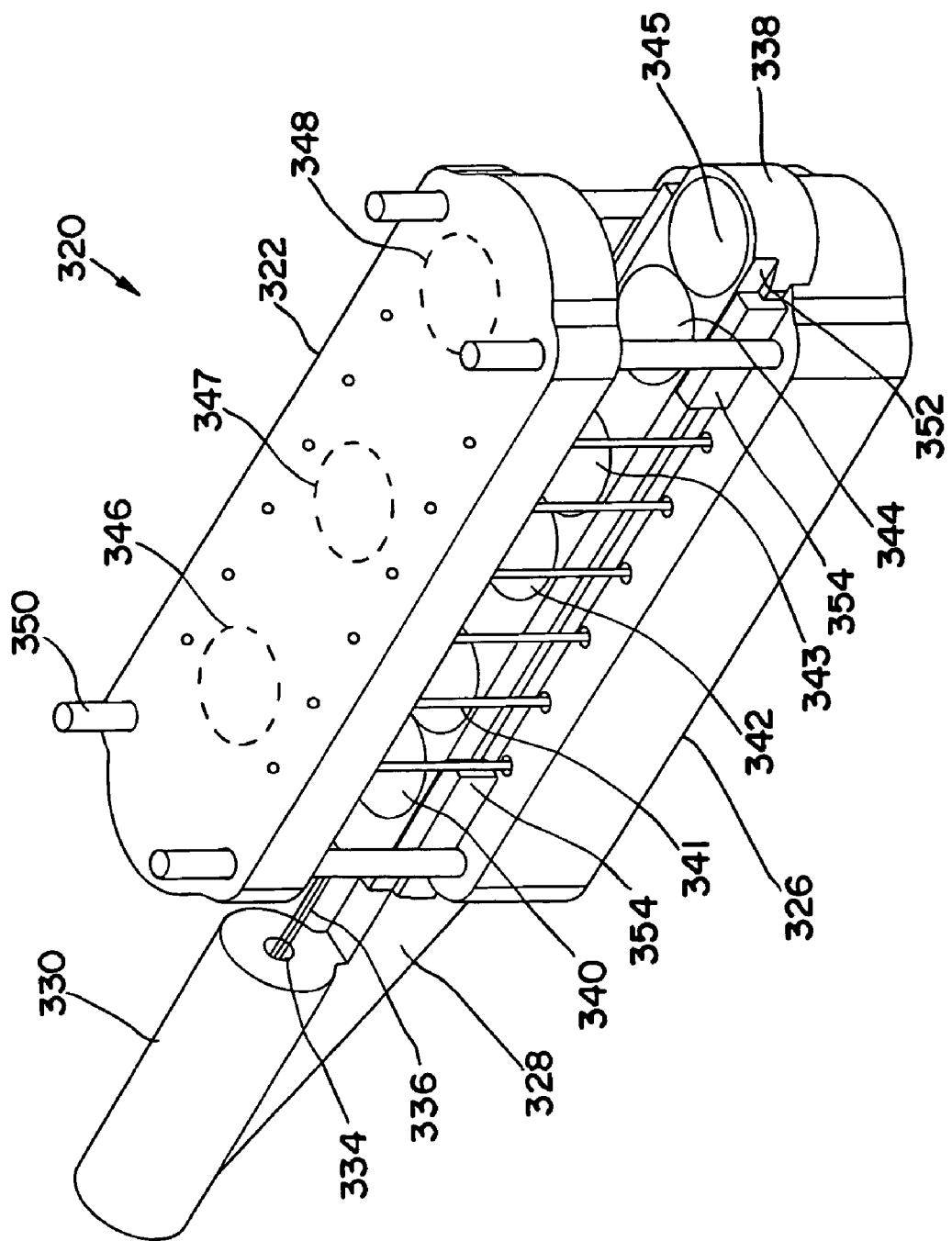
FIG. 14 is a perspective view of the distal injection head of FIG. 13.

FIGS. 13 and 14 illustrate another distal injection head 320, also employing magnets. While distal injection device 260 of FIG. 12 employed magnets acting in repulsion to bias the first and second bodies apart, distal injection head 320 employs magnets to drive the first and second bodies both apart and together. Distal injection device 320 includes a first body 322, and a second body 324 including a second body distal portion 326, an intermediate strut or brace portion 328, and a proximal tube portion 330. Proximal tube 330 may be seen to include a lumen 334 therethrough, terminating in a proximal port 332. Second body distal portion 326 can act as a vacuum plate in some embodiments. In the embodiment illustrated, second body distal portion 326 includes vacuum pods 61 and vacuum lumen 65, as previously discussed. Second body 324 includes guideposts 350 fixedly secured to second body distal portion 326. Guideposts 350 are slidably received through first body 322.

First body 322 may be seen to include three magnets, 346, 347, and 348 disposed therein. In the example illustrated, each of the three magnets is oriented to have the positive pole facing downward, toward second body 324. Distal injection head 320 also includes a longitudinally slideable third member 338 secured to a shaft 336 that is slidably received through lumen 334. In FIG. 14, longitudinally slideable member 338 may be seen to have a lip 352 and a corresponding guide 354 secured to second body distal portion 326. Longitudinally slideable member 338 is slidably secured to second body distal portion 326, and is shown in a far, distal position. Slideable member 338 may be seen to include three pairs of alternating polarity magnets disposed beneath magnets 346, 347, and 348. In the example illustrated, three magnets, 340, 342, and 344 are shown having the positive pole facing upward, and repulsing the positive pole of magnets 346, 347, and 348. Longitudinally slideable member 338 also carries three magnets 341, 343, and 345, having the negative pole facing upwards. The positive and negative polarities of the upward facing magnets are longitudinally offset and alternating in the example illustrated.

Inspection of FIG. 13 shows that proximally retracting shaft 336 through lumen 334 will proximally retract longitudinally slideable member 338, thereby carrying negative polarity magnets 341, 343, and 345 beneath magnets 346, 347, and 348, respectively. This will act to bring the opposite polarity magnet faces closer to each other and will act to drive first body 322 downward against second body distal portion 326. Similarly, distally advancing shaft 336 and longitudinally slideable member 338 acts to bring the same polarity magnet poles opposite each other, acting to drive first body 332 away from second body distal portion 326. These attracting and repulsing forces act to drive needles 68 into tissue, and retract the needles from the tissue, respectively. The use of rare earth magnets can provide a substantial amount of driving and repulsing force in a small volume.

FIGS. 15A and 15B illustrate one needle 400 that can be used in conjunction with the present invention. Needle 400 includes generally a proximal region 402, a shoulder 404, a beveled, distal region 406, a discharge orifice 410, and a sharp end at 408. Needles used in conjunction with the present invention are preferably smaller in size than about a 24-gauge needle, preferably smaller than a 25-gauge needle, and most preferably about a 27-gauge needle for cardiac applications. Applicants believe that needles of a substantially small size, for example, about 27 gauge, allow for penetrating well into the myocardium, while not presenting any problem with bleeding. In one embodiment, the needle is about 0.5 inches in length, having about 0.40 inch between shoulder 404 and sharp distal end 408. Collar 404 can be about 0.010 inch in length in some embodiments. Needle 400 can have an outer diameter of about 0.016 inch, and an inner, lumen diameter of about 0.008 inch. As illustrated in FIGS. 15A and 15B, needle 400 has only a single, distal injection orifice.

FIGS. 16A and 16B illustrate another needle 420 having eight side holes 430 formed in a distal region of the needle. Needle 420 includes generally a proximal region 422, a shoulder 424, a closed distal region 426, and a sharp distal tip 428. Needle 420 may be seen to have numerous side holes 430 formed in the distal region. In one embodiment, four side holes are formed in the needle. In another embodiment, eight side holes are provided through the needle sidewall. In one embodiment, the side holes have an inside diameter of about 0.0005 inch, and are located between about 0.065 inch and about 0.075 inch from distal tip 428. Side holes 430 allow for injection of material at different depths in the tissue to be treated. In one example, material can be injected at several depths of the myocardium simultaneously. In one embodiment, one set of side holes are located about 90 degrees apart, with a second set of side holes longitudinally offset, and radially offset by about 45 degrees from the first set of four side holes. Needles can be formed from stainless steel or other materials well known to those skilled in the art. The side holes can be formed by methods well known to those skilled in the art, such as laser drilling/cutting, wire EDM, traditional EDM, micro drilling, or water jet cutting. The dimensions of needle 420 can be as described with respect to needle 400 of FIGS. 15A and 15B.

FIG. 17 illustrates a mechanism that can be used in conjunction with other embodiments previously illustrated. FIG. 17 includes a portion of a distal injection head 450 having a first body 452 disposed in a spaced apart relationship to a second body 454. As previously discussed with respect to other embodiments, second body 454 can be disposed against the tissue to be injected, and first body 452 used to drive needles into the tissue.

First body 452 has inclined cam surfaces 455 that lie at an angle relative to the longitudinal plane of first body 452. First body 452 also includes substantially level, planar high portions 456 that are not substantially inclined with respect to the plane of first body 452 or the plane of second body 454.

First body 452 may also be seen to have a second set of lower non-inclined regions 458 that are not inclined with respect to the injection plane. Thus, extending from distal to proximal, the underside of first body 452 includes a non-inclined portion 456, an inclined portion 455 extending downward, followed by a non-inclined portion 458. Spring-loaded needles 460 may also be seen in FIG. 17. Spring-loaded needles 460 include generally a cam follower head 462, including a non-inclined portion 464 and an inclined portion 466. Spring-loaded needles 460 further include a shaft 468 terminating in a sharp, distal point 470 and having a compression spring 474 disposed about needle shaft 468, between second body 454 and cam follower head 462. Inspection of FIG. 17 shows that distally advancing first body 452 will cause first body inclined portion 455 to bear against spring-loaded needle cam follower head inclined portion 466, acting to drive needle distal tip 470 downward. As the needles are biased by compression springs 474, proximally retracting first body 452 will allow needles 468 to retract from the tissue.

FIG. 18 illustrates second body 454 and spring-loaded needle 460 in greater detail. Spring-loaded needle 460 is shown in the extended, injecting position. Needle shaft 468 may be seen to include a side hole or entry orifice 480 through the sidewall of the needle and an injection orifice 471. Second body 454 may be seen to have a fluid, injection manifold or lumen 482 disposed through second body 454. When spring-loaded needle 460 is in the depressed configuration, fluid may be injected through fluid supply lumen 482, through needle entry orifice 480, and then out needle distal orifice 471. The fluid supply system illustrated in FIG. 18 may be used in conjunction with any of the embodiments illustrated in the present application. Specifically, a fluid supply lumen or channel may be provided in the second body distal portion or second body vacuum plate in any of the embodiments illustrated in the present application. Fluid may also be supplied in a more conventional manner, being supplied by a manifold supplying the proximal ends of the needles from within the first body, or needle plate in any of the embodiments illustrated in the present application.

Figure 19:
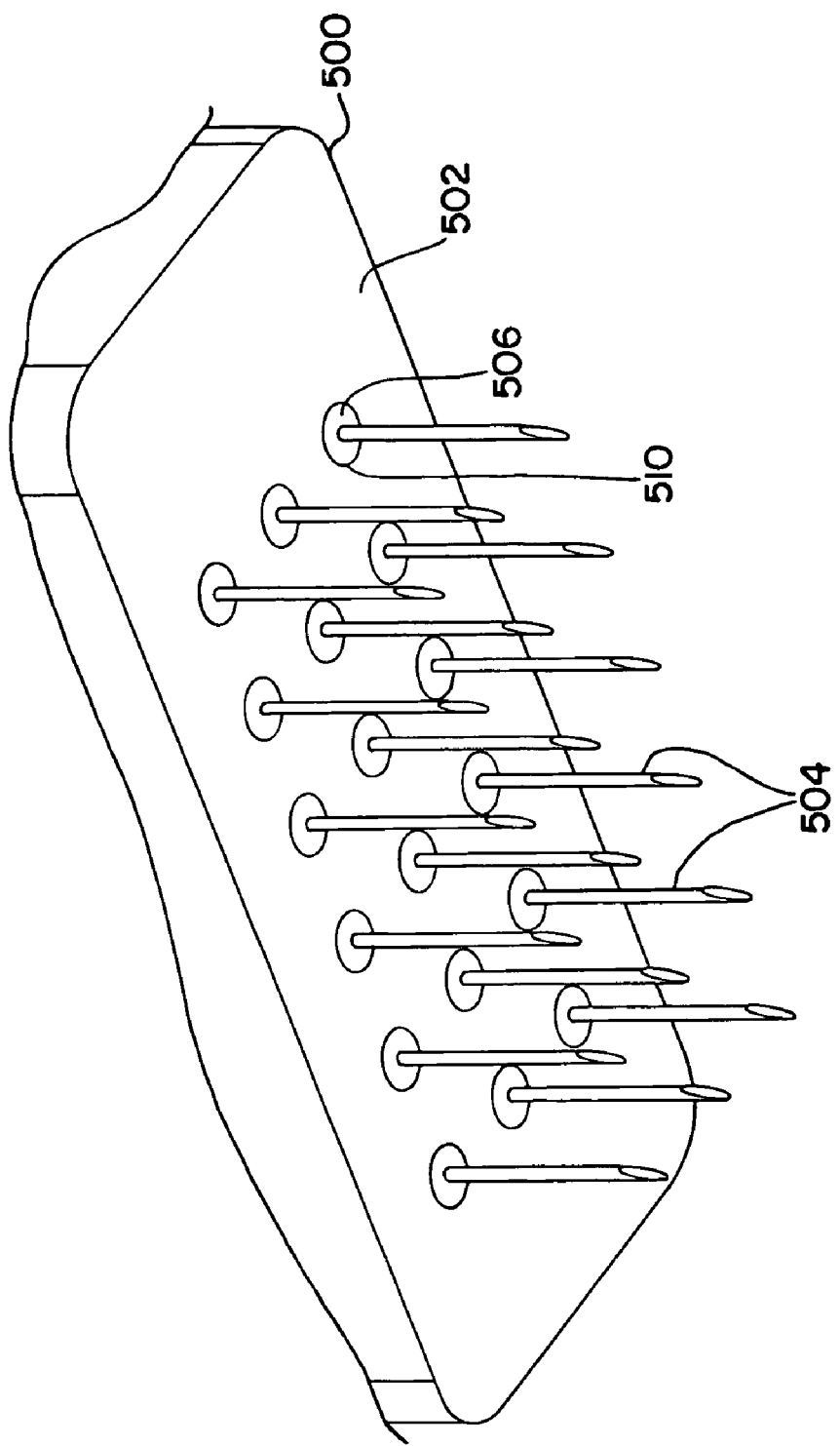
FIG. 19 is a fragmentary perspective view of a second body, tissue-contacting surface having several needles secured to needle holders that are removably secured in the second body.

FIG. 19 illustrates a first body 500 having a surface 502 which includes several holes 510 having needle holders 506 secured within. Needle holders 506 have needles 504 secured within the holders. The needle holders can be removably secured to first body 500 to allow adding and removing needles to the body. Needles, together with the needle holders, can be added or removed to vary the number, pattern, and depth of needles to be used for a particular procedure. In some devices, the needles may be removed and the injection head re-used with different needles in another procedure. Unused openings in surface 502 can be plugged with blanks or solid screws.

Figure 20:
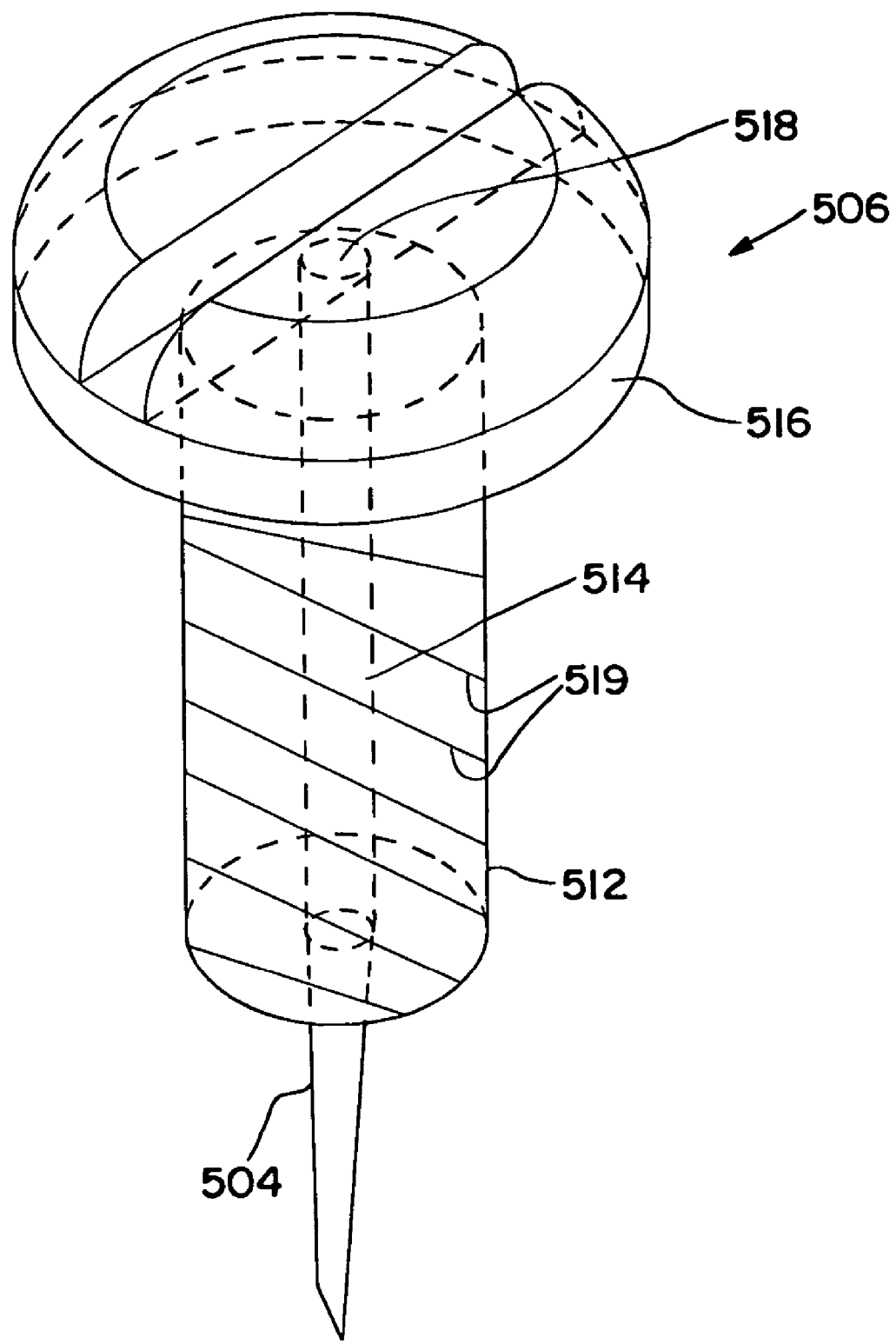
FIG. 20 is a perspective, cut-away view of one threaded screw holder of FIG. 19, having a central longitudinal bore within.

FIG. 20 illustrates needle holder 506 in greater detail. Needle holder 506 includes a cylindrical body 512 having a slotted head 516. A bore 514 extends from a top port 518 through the length of screw holder 506, and has needle 504 fixedly secured within. In the embodiment illustrated, needle holder 506 is threaded at 519, to allow the needle holder to be screwed into the top portion of first body 500 while providing fluid entry to hollow needle 504 through top port 518.

Needle holder 506 can be made by taking a #4 screw having 40 threads per inch, forming bore 514 with electron discharge machining (EDM) or laser welding, then inserting hollow needle 504 into the bore. Needle 504 can be secured to needle holder 506 using epoxy, sliver solder, or a laser weld.

Figure 21:
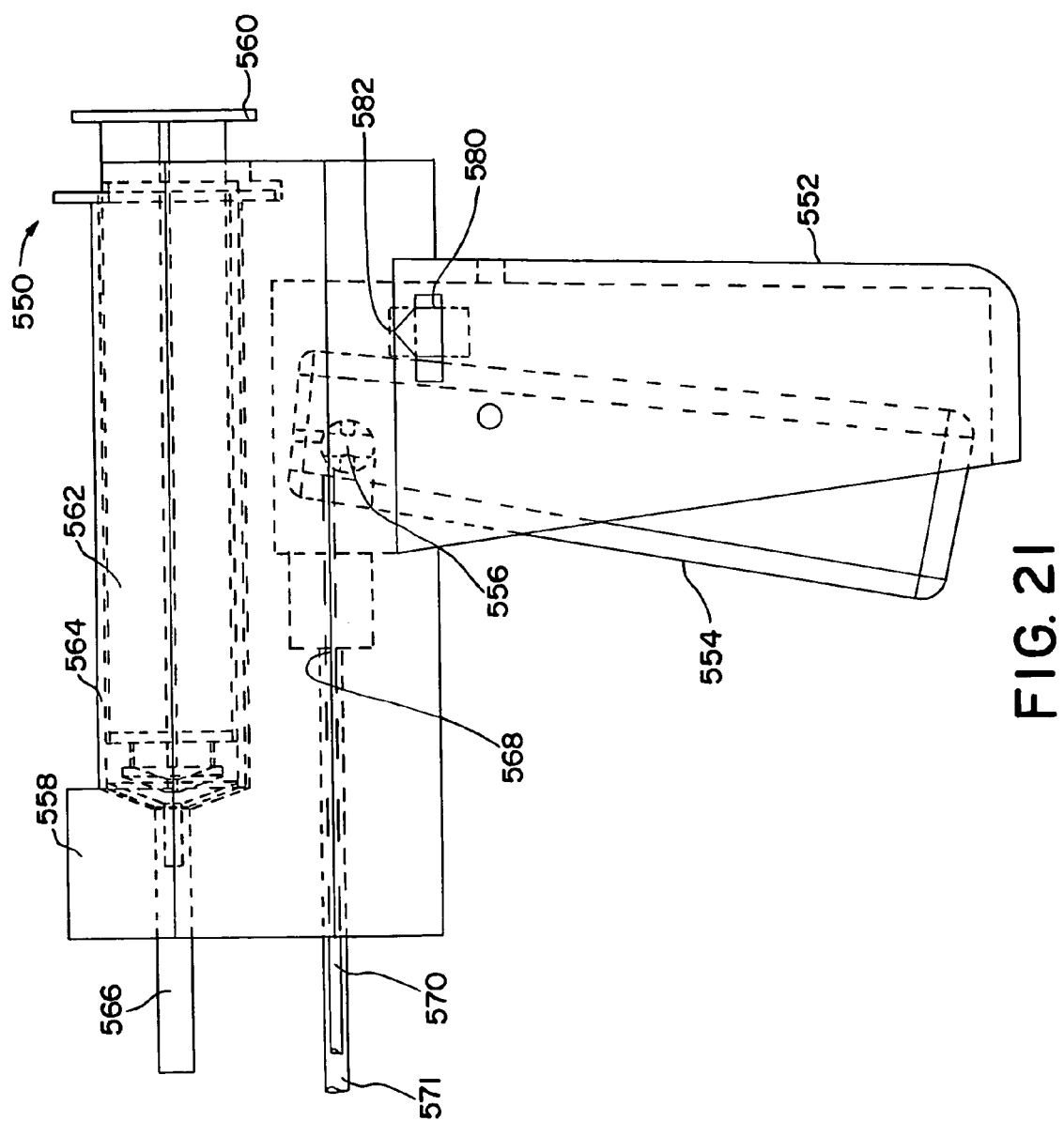
FIG. 21 is a side view of one proximal handle that can be used to supply energy along the elongate shaft and provide fluid for injection along the elongate shaft.

FIG. 21 illustrates a handle 550 that can be used in conjunction with many of the embodiments of the present invention. Handle 550 includes generally a stationary handle portion 552, an actuator lever 554 pivotally mounted about pivot point 556, and a housing or barrel 558. Handle 550 includes a drive cable 570 slideably disposed within a cable sheath 571. Drive cable 570 is coupled to actuator lever 554 at 568. Actuator lever 554, together with drive cable 570 and cable sheath 571 can provide the longitudinal motion and energy for actuating the transverse, needle driving motion described previously with respect to many embodiments of the present invention. A longitudinally slidable depth indicating member 580 may be seen, that can be distally biased and include a pointer 582. Handle 554 bears against depth indicator 580, such that pulling handle 554 extends drive cable 570 and drives the needles. Pulling handle 554 also allows biased depth indicator 580 and pointer 582 to slide forward, to provide a proximal indication of the degree of needle extension.

A syringe mechanism 560 may be seen to include a plunger 562 disposed within a bore or barrel 564. Plunger 562 is in fluid communication with a fluid tube 566. One syringe may be used to provide injectable material, for example biologic agents to be injected into the tissue. Some embodiments include a second syringe or other pressurized fluid mechanism for providing pressure and vacuum to inflate and deflate the envelopes, balloons, and bellows described previously in the present application.

Figure 22:
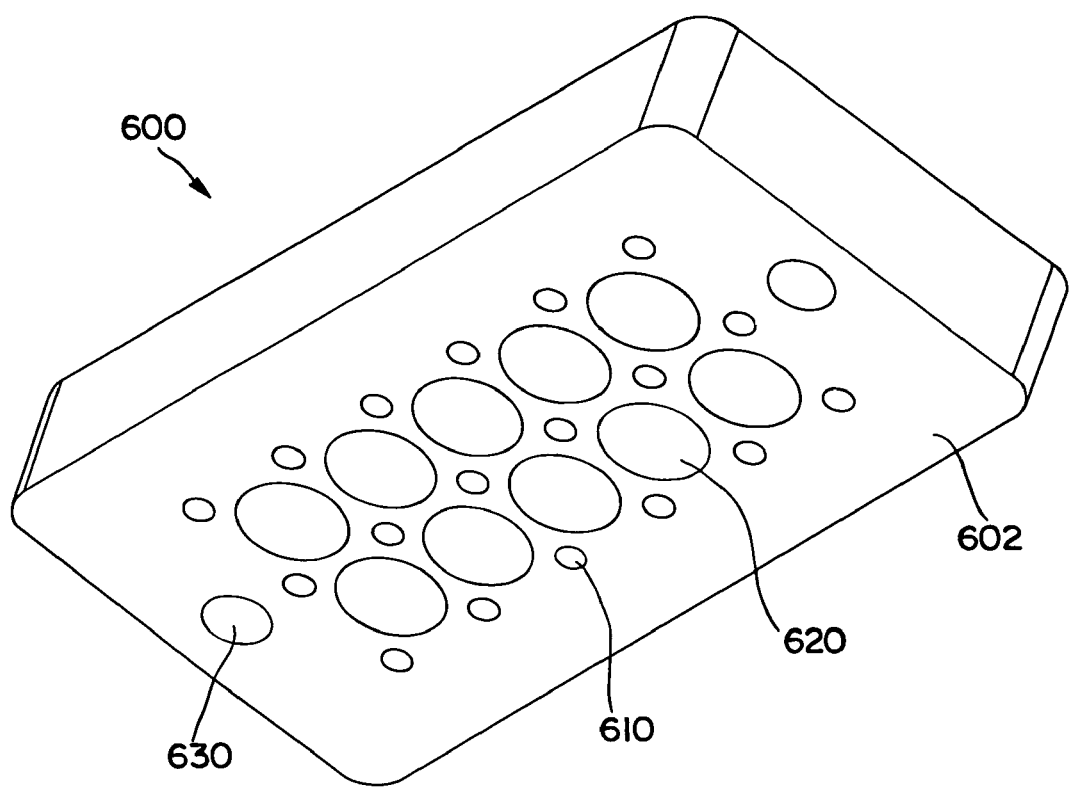
FIG. 22 is a bottom, perspective view of an interstitial injection device second body having needle receiving holes and a sensor.

FIG. 22 illustrates one embodiment of a second body 600 of a distal injection head. Second body 600 has a tissue-contacting surface 602 for contacting tissue. Tissue contacting surface 602 includes one or more holes 610 for slidably receiving one or more needles (not shown) and vacuum suction pods 620. The distal injection head may include one or more sensors, for example, located on the first body and/or the second body. The one or more sensors may be tissue depth sensors for determining the depth of tissue adjacent the distal injection head. The one or more depth sensors may be used to control the depth of needle penetration into the tissue. In this way, the needle penetration depth can be controlled, for example, according to the thickness of tissue, e.g., tissue of a heart chamber wall. In some embodiments (as shown in FIG. 22), one or more sensors 630 may be located on the tissue-contacting surface of second body 600.

The one or more sensors may comprise one or more sensing electrodes. The one or more sensing electrodes may be used to control the delivery of one or more medical agents. The one or more sensors may be used to determine when the distal injection head contacts tissue. For example, a pair of electrodes located on the tissue-contacting surface of the second body may be used to sense when the second body has made contact with tissue. An indicator may then be used to alert the physician that the distal injection head has made contact with tissue thereby allowing the physician to activate suction and/or inject the needles into the tissue. A variety of indicators, e.g., visual or audible, may be used to indicate to the physician that tissue contact has been made.

Figure 23:
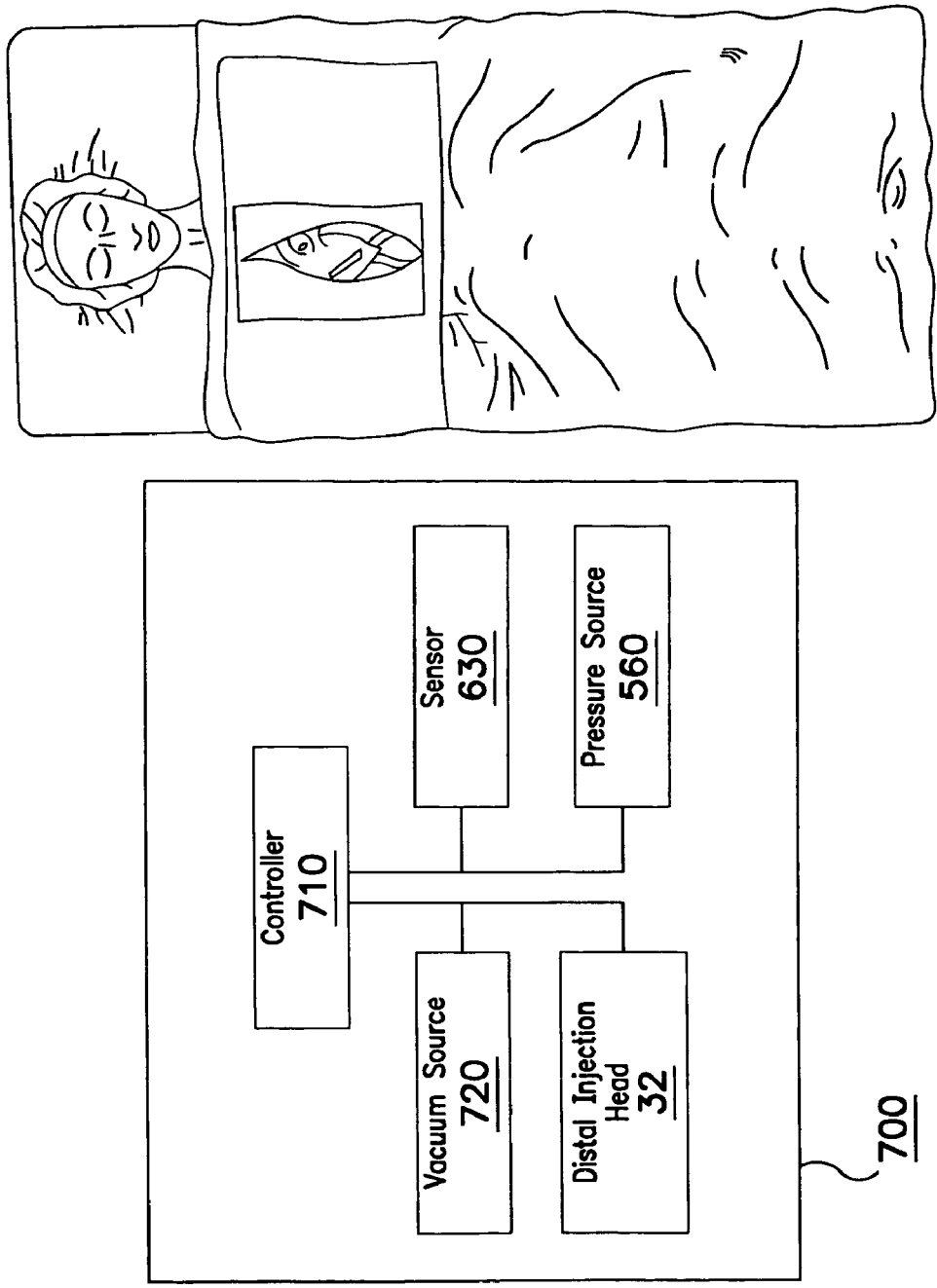
FIG. 23 is a schematic view of a system that can control an interstitial injection device.

FIG. 23 illustrates a system 700 according to the present invention. In one embodiment of the present invention, the one or more sensors may be used to control suction to vacuum suction pods 620. For example, a controller 710 may accept a trigger signal from sensors 630 and in-turn will activate suction to the device from vacuum source 720. Controller 710 may also accept a signal from a vacuum sensor or vacuum switch of vacuum source 720 and activate alarms if vacuum is not within a specific range.

In one embodiment of the present invention, controller 710 may be used to control one or more functions, elements or components of system 700. For example, controller 710 may control a vacuum source 720, distal injection head 32, e.g., injection of needles into tissue, and/or pressure source 560, e.g., injection of one or more medical agents into tissue. For example, controller 710 may accept a trigger signal from sensor 630 and in-turn will control a vacuum source, control delivery or injection of needles into the tissue and/or control delivery or injection of one or more medical agents into the tissue.

Controller 710 may incorporate any suitable processor. Controller 710 may be used to gather and process information from one or more sensors of the system. For example, controller 710 may be used to gather and process information from sensor 630. Controller 710 may incorporate one or more switches to facilitate regulation of the various components by the operator. The switches may be, for example, hand switches, foot switches, and/or a voice-activated switches comprising voice-recognition technologies. Controller 710 may have different modes, e.g., a standby mode, an automatic mode and/or a manual mode. Indicator lights may be used to indicate the mode of operation selected and if the system has malfunctioned. In one embodiment of the present invention, a system malfunction may trigger a flashing light and/or an audible alarm.

On power up, the controller 710 may perform one or more tests. For example, controller 710 may perform a self-test on itself and/or the sensors, switches, valves and/or devices connected to it. If controller 710 detects a malfunction, visual and/or audible alarms may be activated. Controller 710 may be designed to detect failures during operation and set off visual and/or audible alarms if so desired.

Controller 710 may be powered by AC power, e.g., 90 to 264 VAC, 50 or 60 Hz, or by a primary cell or rechargeable battery pack. It may be equipped with one or more fuses. Controller 710 may supply regulated voltage to one or more sensors, indicator lights, and/or audible alarms. Controller 710 may be designed to detect under/over voltage and shut off power to devices and sound an alarm.

Controller 710 may include an electronics enclosure that encloses one or more circuit boards and/or processors. The enclosure may have a front panel for one or more mounted switches, gauges, displays, and/or indicator lights, e.g., a power switch with indicator light. The enclosure may also include audio feedback system for sounding one or more alarms. The enclosure may include one or more entry points for a power cord and/or connectors for cables, e.g., cables from one or more sensors. The enclosure may be mountable onto a pole or be free standing. The enclosure may contain part or all of the power supply, e.g., a battery pack.

Controller 710 may be designed such that it will tolerate or disable itself in a safe mode if a sensor, electronic, and/or mechanical failure occurs. In addition, controller 710 may be designed to remain functional if, for example, the hospital electrical power or the hospital vacuum system fails. There are several modes in which the electrical power can fail, from a local failure in an individual operating room to a total hospital failure that disables the vacuum system.

In one embodiment of the present invention, the front panel or user interface of controller 710 may provide a place for the user to turn the power on and/or off, to provide the user the ability to select the operating mode, to provide the user the ability to control suction, to provide the user the ability to control needle insertion, and/or to provide the user the ability to mute any audible alarms. Controller 710 may accept inputs from a keypad located on the front panel and/or a reset button on a back panel. In addition, the user interface may provide a place for displaying one or more visual alarms. The circuitry of controller 710 may contain, for example, all of the necessary electronic components for processing signals from the system's sensors, e.g., contact sensors 620, controlling suction and/or power to the distal injection head, driving visual displays, visual alarms and/or audible alarms on the user interface, and/or handling the power supply and/or battery backup.

In one embodiment of the present invention, distinct visual and/or audible alerts inform the user, for example, that suction is on or off, the needles are deployed or retracted, that one or more medical agents are being delivered or have been delivered, and/or that the instrument is no longer operable.

In one embodiment of the present invention, the user interface may include one or more LCDs for displaying messages as well as one or more LEDs for visual warnings and/or alarms. Preferably, display information is visible, under normal indoor lighting conditions, from at least 10 feet away and audible alarms have a 2-minute mute capability with visual alert uninterrupted. Preferably, depending on the operating status, indicator lights will be off or flash. A flashing yellow light may be used to indicate a warning condition is occurring. A flashing red light may be used to indicate an alarm condition is occurring. The audible alarms may be monotone or varying frequency.

In one embodiment one or more tissue activated switches and/or sensors may be coupled to vacuum source 720 for turning on or modulating suction to the distal injection head. For example, when one or more sensors and/or switches determine distal injection head contacts tissue suction may be activated. The one or more sensors may be one or more electrical sensors, fiber optic sensors, chemical sensors, mechanical sensors and/or proximity sensors that measure conductance. The one or more switches may be one or more electrical, chemical and/or mechanical switches. For example, sensors 630 may be replaced with one or more small mechanically activated switches. When the mechanical switches are pushed against tissue they become activated thereby turning on suction to the distal injection head. In addition, sensors that can identify different tissue types may be used. For example, fatty tissue has different impedance than vessel wall tissue, therefore impedance sensors may be used to identify fatty tissue from vessel wall tissue. Sensors designed to sense difference in impedance may be used to change the amount of energy supplied to the distal injection head.

In one embodiment of the present invention, the delivery of medical agents from the distal injection head may be enhanced via iontophoresis. In general, the delivery of ionized drugs may be enhanced via a small current applied across two electrodes. Positive ions may be introduced into the tissues from the positive pole, or negative ions from the negative pole. The use of iontophoresis may markedly facilitate the transport of certain ionized drug molecules through tissue. For example, lidocaine hydrochloride may be applied to the heart via the distal injection head. Sensors 630 located on the tissue-contacting surface of second body 600 may comprise a positive electrode and a negative electrode. These electrodes may be used for iontophoresis. Current may be applied between the two electrodes, e.g., between the positive electrode and the negative electrode.

In one embodiment of the present invention, one or more electrodes located on the tissue-contacting surface of second body 600 may be used as stimulation electrodes, e.g., to pace the heart during delivery of one or more medical agents. For example, controller 710 may supply stimulation energy to the one or more electrodes for pacing cardiac tissue. One or more sensors 630 may be used to sense contractions of the heart, thereby allowing the delivery of medical agents to be timed with cardiac contractions. For example, it may be desirable to deliver one or more medical agents between contractions of the heart.

Cardiac contraction sensors may be any suitable sensor, e.g., an electrical sensor, a chemical sensor or a biosensor, for detecting one or more signals indicative of a cardiac contraction or heartbeat. In one embodiment, the cardiac contraction sensor may be coupled to controller 710.

In one embodiment, sensor 630 may be used to monitor the electrical activity of the heart by picking up and amplifying electrical signals from the heart and displaying a visual output and/or providing an audio output. For example, the output may be displayed on a display interface of controller 710. The surgeon may check this output to determine the optimal time to inject the needles and/or medical agents into the tissue.

A cardiac contraction sensor may be a sensor that detects cardiac depolarizations. The electrical signal generated by the sinus node of the heart causes the atria to contract to force blood into the ventricles. After a brief delay, the ventricles contract to force blood out through the body. The contraction of the ventricles is reflected by the passage of a depolarization wavefront through the heart muscle. If a depolarization is sensed, a beat is likely to occur. One such depolarization sensor is disclosed in U.S. Pat. No. 5,156,149 entitled "Sensor for Detecting Cardiac Depolarizations Particularly Adapted for use in a Cardiac Pacemaker", Oct. 2, 1992, to inventor Hudrlik. This patent is assigned to Medtronic, Inc. and is incorporated herein by reference.

A cardiac contraction sensor may be coupled to a cardiac stimulator or controller 710 which may act as a cardiac stimulator. A cardiac contraction sensor may be an apparatus that senses power levels of depolarizations in heart tissue. Such a sensor may be used to distinguish between normally conducted and ectopic heart beats while the heart is beating or may be used to sense an imminent heart beat while the heart is slowed or substantially stilled during a medical procedure. One apparatus that may serve as such a sensor is disclosed in U.S. Pat. No. 5,411,529 entitled "Waveform Discriminator for Cardiac Stimulation Devices", May 2, 1995, to inventor Hurdlik. This patent is assigned to Medtronic, Inc. and is incorporated herein by reference. Other suitable sensors may also serve as cardiac contraction sensor.

The devices according to the present invention can be used in several methods to deliver material to tissue. In one, minithoracotomy method, a patient is intubated with a double-lumen endobronchial tube that allows selective ventilation or deflation of the right and left lungs. The left lung is deflated, thereby helping to provide access to the surface of the heart. A left anterior thoracotomy or incision is created over an intercostal space, preferably the 4th intercostal space. An alternative intercostal space may be used depending on the patient's physiology, e.g., the 5th intercostal space. The thoracotomy should be as anterior and medial as possible without removing cartilage. A two-inch incision is preferable, however the size of the incision may vary depending on the patient. The ribs, adjacent the incision, may be spread, preferably two-inches or less, using a small rib retractor or spreader to allow adequate access into the chest. If desired, a retractor may be used to spread the ribs both horizontally and vertically. Next, the pericardium is opened directly under the incision. Dissection through fat may be required to reach the pericardium. The pericardium may be opened by a number of different techniques. In one embodiment of the present invention, the pericardium may be opened by tenting it with graspers and then cutting it with scissors. In an alternative embodiment of the present invention, a device as disclosed in either U.S. Pat. No. 5,931,810 or U.S. Pat. No. 6,156,009 both to Grabeck may be used to access the pericardial space. In addition, devices as disclosed in U.S. Pat. No. 5,972,013 to Schmidt, U.S. Pat. No. 5,827,216 to Igo, et al., U.S. Pat. No. 6,162,195 to Igo, et al., U.S. Pat. No. 4,991,578 to Cohen and U.S. Pat. No. 5,336,252 to Cohen may be used, for example, to access the pericardial space. These patents are incorporated herein by reference.

In one embodiment of the present invention, one or more devices may be used within the pericardial space for creating space and visualizing the surface of the heart. For example, a device comprising a rigid rod with a light may be used to push on the interior of the pericardium and to move the lung laterally if desired. Another device comprising a flat malleable spatula may be used to rotate the heart and expose the posterior lateral portion of the heart if desired. The spatula device may be bent or formed into whatever shape is required to move and rotate the heart.

In one embodiment of the present invention, a suction positioning device as described in U.S. Pat. No. 6,447,443 to Keogh et al., incorporated herein by reference, may be used to move the heart around and/or hold the pericardium out of the way. The positioning device may be used to engage the heart and to position the heart into a non-physiological orientation.

Upon gaining access to the epicardial surface of the heart, the injection head and shaft are inserted through the mini-thoracotomy. The distal injection head is then placed against the surface of the heart. Suction may be applied prior to the injection of needles into the tissue. Following delivery of one or more medical agents, the needles are retracted and suction, if used, may be turned off. The heart may be repositioned is desired, for example, with a suction positioning device. The distal injection head may then be repositioned for additional delivery of one or more medical agents or the head and shaft may be removed from the patient. All incision may then be closed using standard techniques. If the pleura is closed, a small tube for drainage may be left in place and removed the same day as surgery. If the pleura is open, a larger tube may be left in place for 24 hours.

In one, thoroscopic method, a patient is intubated with a double-lumen endobronchial tube that allows selective ventilation or deflation of the right and left lungs. The left lung is deflated, thereby helping to provide access to the surface of the heart. The patient is rotated approximately 30° with the left side up. The left arm is placed below and behind the patient so as not to interfere with tool manipulation during the delivery of one or more medical agents. While port positions depend to a large extent on heart size and position, in general a $7^{th}$ and $5^{th}$ space mid (to posterior) axillary port for tools and a $3^{rd}$ space anterior axillary port for the scope is preferable. A variety of endoscopes or thoracoscopes may be used including a 30 degree offset viewing scope or a straight ahead viewing scope. In general, short 10 to 12 mm ports are sufficient. A soft 20 mm port-with an oval cross section sometimes allows for two tools in the port without compromising patient morbidity.

The pericardium may be opened by a number of different techniques. In one embodiment of the present invention, the pericardium may be opened by tenting it with graspers and then cutting it with scissors. In an alternative embodiment of the present invention, a device as disclosed in either U.S. Pat. No. 5,931,810 or U.S. Pat. No. 6,156,009 both to Grabeck may be used to access the pericardial space. In addition, devices as disclosed in U.S. Pat. No. 5,972,013 to Schmidt, U.S. Pat. No. 5,827,216 to Igo, et al., U.S. Pat. No. 6,162,195 to Igo, et al., U.S. Pat. No. 4,991,578 to Cohen and U.S. Pat. No. 5,336,252 to Cohen may be used, for example, to access the pericardial space. Upon gaining access to the epicardial surface of the heart, the injection head and shaft are inserted through an appropriate port. The distal injection head is then placed against the surface of the heart. Suction may be applied prior to the injection of needles into the tissue. Following delivery of one or more medical agents, the needles are retracted and suction, if used, is turned off. The distal injection head may then be repositioned for additional delivery of one or more medical agents or the head and shaft may be removed from the patient. All incisions may then be closed using standard techniques. Some methods may utilize insufflation, in which the incision or port is sealed about the device shaft and the interior of the thorax pressurized.

In one, sternotomy method, the device may be inserted through an incision made through the sternum. In yet another method, a xiphoid incision method, an incision is made below the sternum and the injection head is then inserted through the incision. The term "xiphoid incision" refers to a surgical incision proximate to, but not necessarily directly above, the xiphoid appendage. The xiphoid incision of the invention provides a surgical field and access site to the heart that extends through an opening beneath the sternum and preferably immediately beneath the lowest rib.

A vertical skin incision is made above the xiphoid process and the center of the xiphoid appendage is transected. Because the xiphoid appendage is cartilaginous, the appendage does not have to be removed and the sternum does not have to be transected. The total length of the xiphoid incision depends on length of xiphoid appendage, i.e., longer xiphoids are less likely to require any cutting into the sternum. The maximum incision is preferably approximately 6-7 cm from below the tip of the xiphoid appendage upwards towards the patient's head. The incision may be extended downward below the xiphoid appendage to the extent necessary to provide an adequate surgical field, but as noted above, the maximum length should not greatly exceed 6-7 cm. The incision may be strictly vertical or may be slightly curved, following the outline of the butt of either the right or left rib cage. In most cases, a curved incision will follow the lower left rib. An approximately 1 cm incision may be made in the pericardium to accommodate insertion of a surgical scope. The scope preferably has a flexible housing and at least a 16× magnification. Insertion of the scope through the pericardial incision allows the surgeon to inspect the epicardial surface of the heart thereby allowing the physician to plan the procedure depending on the clinical status of the individual patient. At this point, the surgeon can confirm that a xiphoid access is appropriate for the particular procedure to be performed.

A vertically offsetting retractor or access platform may be used to engage a portion of the rib cage capable of lifting at least one rib and preferably more than one rib and the sternum, see U.S. Pat. No. 6,199,556 to Benetti et al. This patent is incorporated herein by reference. The term "offsetting" herein is used to describe a manipulation of at least one rib that provides access to the thoracic cavity via the xiphoid incision, generally described herein as "xiphoid access." Typically, the vertical offsetting procedure comprises engaging the lowermost rib with an offsetting retractor or access platform and lifting at least a portion of the lowermost ribs. This may be accomplished by simultaneously applying force at one or more points about the chest and pelvis, and preferably includes at least a mechanical force applied vertically to orient at least a portion of the lower region of the sternum and rib cage relative to the remainder of the body below the rib cage. As noted, this orientation is most readily achieved by lifting one half of the lower edge of the rib cage, adjacent to the xiphoid appendage using a specially designed surgical retractor. Although retraction devices such as those described in U.S. Pat. No. 5,730,757 are preferred, other more conventional devices could be adapted, see for example U.S. Pat. Nos. 5,026,779, 4,726,358 and 4,852,552. These patents are incorporated herein by reference. Collectively, these devices can provide access to a beating heart via a xiphoid incision and comprise means for offset retraction of the lower rib cage.

Since the size of the incision is preferably minimized in a xiphoid procedure, an organ or tissue positioner may advantageously be used to retract or reposition tissue or internal organs at the site of the incision or inside the thoracic cavity near the site of the surgery. The positioner or retractor may be of any conventional mechanical design, or expandable by inflation on manipulation, and is preferably suitable for minimally invasive procedures. Moreover, a tissue or organ positioner may be affixed to the offsetting retractor during the procedure to maintain access to the surgical field.

Upon gaining access to the epicardial surface of the heart, the injection head and shaft are inserted through the xiphoid incision. The distal injection head is then placed against the surface of the heart. Suction may be applied prior to the injection of needles into the tissue. Following delivery of one or more medical agents, the needles are retracted and suction, if used, may be turned off. The distal injection head may then be repositioned for additional delivery of one or more medical agents or the head and shaft may be removed from the patient. All incisions may then be closed using standard techniques. A small incision may be made below the xiphoid appendage and a drainage tube may be inserted into the pericardium, if the pleura has not been opened, and into the pluera itself if it has been opened. Before finally closing the xyphoid incision, a scope may be used to check the position of the drainage tube, and to check the integrity of the pleura.

The elongate device shaft can be used to position the injection head over the epicardium as desired. In some methods, the device elongate shaft is flexible, and is introduced through a small incision, port or cannula. In some devices, the distal injection head has a thickness of no greater than about 15 millimeters, to allow for insertion between the ribs in an incision having a height of no greater than about 15 millimeters.

Cells suitable for implantation according to the present invention include a wide variety of cells, e.g., undifferentiated contractile cells. Typically, undifferentiated contractile cells differentiate to form muscle cells, however, they can be fibroblasts that have been converted to myoblasts ex vivo, or any of a wide variety of immunologically neutral cells that have been programmed to function as undifferentiated contractile cells. Cells of mesodermal origin that form contractile cells can be injected, and include skeletal muscle cells, heart muscle cells, and smooth muscle cells, as well precursor cells to the cells, such as pluripotent stem cells, embryonic stem cells, mesodermal stem cells, myoblast, fibroblasts, and cardiomyocytes. Suitable cells for use in the present invention can include umbilical cells, and skeletal muscle satellite cells. Suitable cells for implantation also include differentiated cardiac or skeletal cells, such as cardiomyocytes, myotubes and muscle fiber cells, and the like, whether they are autologous, allogeneic or xenogenic, genetically engineered or non-engineered. Mixtures of such cells can also be used. Autologous cells are particularly desirable. The cells are capable of repopulating the infarct zone of the myocardium or capable of establishing health tissue in damaged or diseased myocardial areas or aiding in the angiogenesis process.

Skeletal muscle satellite cells are particularly suitable for use in the present invention because they can differentiate to muscle cells that are capable of contracting in response to electrical stimulation. They are also particularly suitable for use in the present invention because they can be obtained from cell cultures derived from the biopsy samples of the same patient. Biopsy samples contain mature skeletal fibers along with reserve cells surrounding the mature fibers. Once placed in culture, reserve cells proliferate and their numbers quickly increase. These newly cultured cells can be injected back into the heart in and/or near the infarct zone. Once in the heart muscle, the skeletal myoblasts fuse to form multinucleated myotubes having contractile characteristics.

The undifferentiated and/or differentiated contractile cells can be delivered in combination with a delivery vehicle, such as liposomes or a polymeric matrix. Once the undifferentiated and/or differentiated cells form contractile tissue, their function can be further enhanced by metabolically altering them, for example, by inhibiting the formation of myostatin. This increases the number of muscle fibers.

In some methods, the cells are suspended in a liquid, and supplied to the distal injection head through a lumen in a tube. In other methods, the cells or other material is loaded into the needles in plug form, advanced to the target site, and ejected from the needles through the application of pressure to the needles. In one such method, cell material too viscous to flow through an elongate tube is loaded into the needles and discharged through the application of saline to the needles. In one method, a biopsy type sample is contained in the needles and injected under pressure to the target tissue.

Other therapeutic agents can be injected using devices and methods according to the present invention. Specific examples of therapeutic agents used in conjunction with the present invention include proteins, oligonucleotides, ribozymes, anti-sense genes, DNA compacting agents, gene/vector systems, nucleic acids (including recombinant nucleic acids; naked DNA, cDNA, RNA; genomic DNA, cDNA or RNA in a non-infectious vector or in a viral vector which may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic polymers. Other pharmaceutically active materials include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/antimitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitorfurantoin; anesthetic agents such as lidocaine, bupivacaine, and ropivacaine; nitric oxide (NO) donors such as lisidomine, molsidominc, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warafin sodium, Dicumarol, aspirin, prostaglandin inhibitors, platelet inhibitors and tick antiplatelet factors; vascular cell growth promotors such as growth factors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vascoactive mechanisms; survival genes which protect against cell death, such as anti-apoptotic Bcl-2 family factors and Akt kinase; and combinations thereof.

Examples of polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides of the invention can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins useful in the present invention include, without limitation, angiogenic factors and other molecules competent to induce angiogenesis, including acidic and basic fibroblast growth factors, vascular endothelial growth factor, hif-1, epidermal growth factor, transforming growth factor .alpha. and .beta., platelet-derived endothelial growth factor, platelet-derived growth factor, tumor necrosis factor .alpha., hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and d the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

The invention claimed is:

1. A device for injecting a medical agent into tissue, the device comprising:
   an elongate shaft comprising a length, a longitudinal axis, a proximal region and a distal region, wherein the distal region comprises a distal region longitudinal axis;
   a plurality of hollow needles having a sharp distal end, at least one discharge port, a length, and a needle axis along the needle length, wherein the needles are operably coupled to the elongate shaft distal region such that needle axes are substantially perpendicular to the elongate shaft distal region;
   a needle driver coupled to the elongate shaft configured to drive the needles substantially perpendicular to the distal region longitudinal axis and into the tissue; and
   a discharger configured to discharge the agent from the needle discharge ports, wherein the needle driver comprises a first body having the needles fixedly attached thereto and a second body having the needles slidably disposed therethrough, wherein the first body comprises a first side and a second side and wherein the second body comprises a first side and a second side, wherein the first sides are opposite relative to the second sides, and wherein each of the first sides and each of the second sides comprise a distal arm linkage and a proximal arm linkage, wherein the distal and proximal arm linkages comprise a first linkage arm pivotally coupled to the first body and a second linkage arm pivotally coupled to both the second body and to the first linkage arm about a linkage joint, such that urging the distal linkage joints and proximal linkage joints farther apart urges the first and second bodies closer together and urging the distal and proximal linkage joints closer together urges the first and second bodies farther apart, wherein the proximal linkage joints are secured to the elongate shaft, the device further comprising a first elongate member slidably coupled to the elongate shaft and having a first elongate member distal region secured to the distal linkage joint, such that distally sliding the first elongate member relative to the elongate shaft urges the distal and proximal linkage joints further apart and the needles along their needle axes out of the second body, and such that proximally retracting the first elongate member relative to the elongate shaft urges the distal and proximal linkage joints closer together and urges the needles into the second body.

2. The device of claim 1, wherein the first elongate member is slidably disposed within a lumen in the elongate shaft.

3. The device of claim 1, wherein the first elongate member disposed within the elongate shaft and having a first elongate member distal region secured to the distal linkage joint, wherein the first elongate member helically threadably engages at least one of the distal linkage joint and the proximal linkage joint, such that rotating the first elongate member in a first direction urges the distal and proximal linkage joints further apart and the needles along their needle axes out of the second body, such that rotating the first elongate member in a second direction urges the distal and proximal linkage joints closer together and urges the needles toward the second body.

4. A device for injecting a medical agent into tissue, the device comprising:
   an elongate shaft comprising a length, a longitudinal axis, a proximal region and a distal region, wherein the distal region comprises a distal region longitudinal axis;
   a plurality of hollow needles having a sharp distal end, at least one discharge port, a length, and a needle axis along the needle length, wherein the needles are operably coupled to the elongate shaft distal region such that needle axes are substantially perpendicular to the elongate shaft distal region;
   a needle driver coupled to the elongate shaft configured to drive the needles substantially perpendicular to the distal region longitudinal axis and into the tissue; and
   a discharger configured to discharge the agent from the needle discharge ports, wherein the needle driver comprises a first body having the needles fixedly attached thereto and a second body having the needles slidably disposed therethrough, wherein the second body comprises a rack fixedly coupled to the second body, and wherein the device further comprises a pinion rotatably coupled to the first body and having teeth engaging the rack such that rotating the pinion in a first direction urges the first and second bodies closer together and rotating the pinion in a second direction urges the first and second bodies farther apart.

5. The device of claim 4, wherein the first elongate member is rotatably disposed within the elongate shaft.

6. A device for injecting a medical agent into tissue, the device comprising:
    an elongate shaft comprising a length, a longitudinal axis, a proximal region and a distal region, wherein the distal region comprises a distal region longitudinal axis;
    a plurality of hollow needles having a sharp distal end, at least one discharge port, a length, and a needle axis along the needle length, wherein the needles are operably coupled to the elongate shaft distal region such that needle axes are substantially perpendicular to the elongate shaft distal region;
    a needle driver coupled to the elongate shaft configured to drive the needles substantially perpendicular to the distal region longitudinal axis and into the tissue; and
    a discharger configured to discharge the agent from the needle discharge ports, wherein the needle driver comprises a first body having the needles fixedly attached thereto and a second body having the needles slidably disposed therethrough, wherein the first and second bodies comprise a first expandable member disposed therebetween such that expanding the first expandable member urges the first and second bodies apart and retracts the needles toward the second body.

7. The device of claim 6, wherein the first expandable member is a fluid inflatable member.

8. The device of claim 7, wherein the fluid inflatable member is coupled to the first and second bodies and is deflatable such that withdrawing fluid from the fluid inflatable member urges the first and second bodies closer together.

9. The device of claim 6, further comprising a second expandable member disposed on the first body away from the second body, such that disposing the second body against the tissue and disposing the second expandable member against a body part urges the first body towards the tissue.

10. The device of claim 9, wherein the second expandable member is a fluid expandable member.

11. A device for injecting a medical agent into tissue, the device comprising:
    an elongate shaft comprising a length, a longitudinal axis, a proximal region and a distal region, wherein the distal region comprises a distal region longitudinal axis;
    a plurality of hollow needles having a sharp distal end, at least one discharge port, a length, and a needle axis along the needle length, wherein the needles are operably coupled to the elongate shaft distal region such that needle axes are substantially perpendicular to the elongate shaft distal region;
    a needle driver coupled to the elongate shaft configured to drive the needles substantially perpendicular to the distal region longitudinal axis and into the tissue; and
    a discharger configured to discharge the agent from the needle discharge ports, wherein the needle driver comprises a first body having the needles fixedly attached thereto and a second body having the needles slidably disposed therethrough, wherein the first body comprises a first magnet, and the second body comprises a second magnet, and wherein the magnets are disposed opposite each other such that the first and second bodies are magnetically biased apart.

12. The device of claim 11, further comprising at least one elongate flexible member fixedly coupled to the first body or the second body and slidably received through the body not fixedly coupled to the flexible member, such that proximally retracting the elongate flexible member urges the first and second bodies closer together.

13. A device for injecting a medical agent into tissue, the device comprising:
    an elongate shaft comprising a length, a longitudinal axis, a proximal region and a distal region, wherein the distal region comprises a distal region longitudinal axis;
    a plurality of hollow needles having a sharp distal end, at least one discharge port, a length, and a needle axis along the needle length, wherein the needles are operably coupled to the elongate shaft distal region such that needle axes are substantially perpendicular to the elongate shaft distal region;
    a needle driver coupled to the elongate shaft configured to drive the needles substantially perpendicular to the distal region longitudinal axis and into the tissue; and
    a discharger configured to discharge the agent from the needle discharge ports, wherein the needle driver comprises a first body having the needles fixedly attached thereto and a second body having the needles slidably disposed therethrough, wherein the first body comprises a first magnet and the second body comprises a second magnet, wherein the magnets are disposed opposite each other such that the first and second bodies are magnetically biased toward each other.

14. A device for injecting a medical agent into tissue, the device comprising:
    an elongate shaft comprising a length, a longitudinal axis, a proximal region and a distal region, wherein the distal region comprises a distal region longitudinal axis;
    a plurality of hollow needles having a sharp distal end, at least one discharge port, a length, and a needle axis along the needle length, wherein the needles are operably coupled to the elongate shaft distal region such that needle axes are substantially perpendicular to the elongate shaft distal region;
    a needle driver coupled to the elongate shaft configured to drive the needles substantially perpendicular to the distal region longitudinal axis and into the tissue; and
    a discharger configured to discharge the agent from the needle discharge ports, wherein the needle driver comprises a first body having the needles fixedly attached thereto and a second body having the needles slidably disposed therethrough, wherein the first body or the second body comprises at least one first magnet facing the body that does not comprise the first magnet, wherein the body that does not comprise the first magnet comprises a second magnet slidably disposed thereon and having an opposite polarity facing the first magnet, such that the first and second magnets have a first position wherein the first magnet attracts the second magnet, and a second position, wherein the first magnet does not attract the second magnet.

15. A device for injecting a medical agent into tissue, the device comprising:
    an elongate shaft comprising a length, a longitudinal axis, a proximal region and a distal region, wherein the distal region comprises a distal region longitudinal axis;
    a plurality of hollow needles having a sharp distal end, at least one discharge port, a length, and a needle axis along the needle length, wherein the needles are operably coupled to the elongate shaft distal region such that needle axes are substantially perpendicular to the elongate shaft distal region;

a needle driver coupled to the elongate shaft configured to drive the needles substantially perpendicular to the distal region longitudinal axis and into the tissue; and a discharger configured to discharge the agent from the needle discharge ports, wherein the needle driver comprises a first body having the needles fixedly attached thereto and a second body having the needles slidably disposed therethrough, wherein the first body or the second body comprises at least one first magnet facing the body that does not comprise the first magnet, wherein the body that does not comprise the first magnet comprises a second magnet slidably disposed thereon and having the same polarity facing the first magnet, such that the first and second magnets have a first position wherein the first magnet repulses the second magnet, and a second position, wherein the first magnet does not repulse the second magnet.

16. The device of claim 15, wherein one of the first and second bodies comprises a third magnet facing the body that does not comprise the third magnet, wherein the third magnet is adjacent to the first or second magnet and has the opposite polarity, wherein, in the first position the third magnet repulses the body that does not comprise the third magnet, and wherein, in the second position, the third magnet is attracted to the body that does not comprise the third magnet.

17. A device for injecting a medical agent into tissue, the device comprising:

an elongate shaft comprising a length, a longitudinal axis, a proximal region and a distal region, wherein the distal region comprises a distal region longitudinal axis;

a plurality of hollow needles having a sharp distal end, at least one discharge port, a length, and a needle axis along the needle length, wherein the needles are operably coupled to the elongate shaft distal region such that needle axes are substantially perpendicular to the elongate shaft distal region;

a needle driver coupled to the elongate shaft configured to drive the needles substantially perpendicular to the distal region longitudinal axis and into the tissue; and a discharger configured to discharge the agent from the needle discharge ports, wherein the needle driver comprises a first body having the needles fixedly attached thereto and a second body having the needles slidably disposed therethrough, wherein the first body comprises a first magnet, the second body comprises a second magnet, and wherein one of the first and second bodies comprises a third magnet, wherein at least one of the three magnets is slidably disposed on its respective body and at least two of the three magnets are adjacent and have opposite polarities such that the three magnets have a first position wherein two of the three magnets attract the first and second body together and a second position wherein two of the three magnets repulse the first and second body apart.

18. A device for injecting a medical agent into tissue, the device comprising:

an elongate shall comprising a length, a longitudinal axis, a proximal region and a distal region, wherein the distal region comprises a distal region longitudinal axis;

a plurality of hollow needles having a sharp distal end, at least one discharge port, a length, and a needle axis along the needle length, wherein the needles are operably coupled to the elongate shaft distal region such that needle axes are substantially perpendicular to the elongate shaft distal region;

a needle driver coupled to the elongate shaft configured to drive the needles substantially perpendicular to the distal region longitudinal axis and into the tissue; and a discharger configured to discharge the agent from the needle discharge ports, wherein the needle driver comprises a first body having the needles fixedly attached thereto and a second body having the needles slidably disposed therethrough, wherein the second body comprises at least one sensor.

19. The device of claim 18, wherein the sensor is coupled to a controller.

20. The device of claim 19, wherein the controller is coupled to a vacuum source.

21. The device of claim 19, wherein the controller is coupled to a needle penetration depth controller.

22. A device for injecting a medical substance into tissue, the device comprising:

a first body comprising a plurality of hollow needles and a first plurality of magnets;

a second body having the plurality of needles slidably received therethrough;

a third body comprising a second plurality of magnets, wherein the third body is slidably disposed on the second body; wherein the first and second plurality of magnets are disposed and have polarities oriented such that the slidable third body has a first position in which the first and third body are magnetically attracted to each other and a second position in which the first and third body are magnetically repulsed from each other, such that sliding the third member can act to pull the first body toward the second body and can also act to push the first body away from the second body.

23. The device of claim 22, wherein the third body has longitudinally adjacent magnet pairs having opposite polarities, such that sliding the third member into the first position brings magnets having opposite facing polarities opposite each other and sliding the third member into the second position brings magnets having the same facing polarities opposite each other.

24. A device for injecting a medical substance into tissue, the device comprising:

a first body having a plurality of hollow needles attached thereto;

a second body having the plurality of needles slidably received therethrough, wherein the second body includes a rack fixedly coupled to the second body, the device further comprising a pinion rotatably coupled to the first body and having teeth engaging the rack such that rotating the pinion in a first direction urges the first and second bodies closer together and rotating the pinion in a second direction urges the first and second bodies farther apart.

25. A device as in claim 24, wherein the plurality of needles have substantially different lengths among the needles.

26. A device for injecting a medical substance into tissue, the device comprising:

a first body having a plurality of hollow needles attached thereto;

a second body having the plurality of needles slidably received therethrough, wherein the first and second bodies have a first expandable member disposed therebetween, such that expanding the first expandable member urges the first and second bodies apart and retracts the needles toward the second body.

27. A device as in claim 26, wherein the first expandable member is a fluid inflatable member.

28. A device as in claim 27, wherein the first inflatable member is coupled to the first and second bodies and is deflatable, such that withdrawing fluid from the first inflatable member urges the first and second bodies closer together.

29. A device as in claim 26, further comprising a second expandable member disposed on the first body facing away from the second body, such that disposing the second body against the tissue and disposing the second expandable member against a body part urges the first body towards the tissue.

30. A device as in claim 29, wherein the second expandable member is a fluid expandable member.

* * * * *

UNITED STATES PATENT AND TRADEMARK OFFICE
CERTIFICATE OF CORRECTION

PATENT NO. : 7,744,562 B2
APPLICATION NO. : 11/545197
DATED : June 29, 2010
INVENTOR(S) : Scott E. Jahns et al.

Page 1 of 1

It is certified that error appears in the above-identified patent and that said Letters Patent is hereby corrected as shown below:

In Column 27, Line 61: Amend claim 35 ...elongate shall comprising... should be ...elongated shaft comprising...

Signed and Sealed this
First Day of May, 2012

David J. Kappos
*Director of the United States Patent and Trademark Office*